(12) United States Patent
Takakura

(10) Patent No.: US 7,713,531 B2
(45) Date of Patent: May 11, 2010

(54) PROTEIN, A GENE ENCODING THEREFOR AND A METHOD OF USING THE SAME

(75) Inventor: Yoshimitsu Takakura, Shizuoka (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

(21) Appl. No.: 12/369,587

(22) Filed: Feb. 11, 2009

(65) Prior Publication Data

US 2009/0187006 A1 Jul. 23, 2009

Related U.S. Application Data

(62) Division of application No. 10/471,422, filed as application No. PCT/JP02/02295 on Mar. 12, 2002.

(30) Foreign Application Priority Data

Mar. 12, 2001 (JP) ............................. 2001-068894

(51) Int. Cl.
*A61K 39/00* (2006.01)
(52) U.S. Cl. .............. 424/184.1; 424/185.1; 424/193.1; 424/274.1; 530/350; 435/69.1; 435/410
(58) Field of Classification Search ........................ None
See application file for complete search history.

(56) References Cited

U.S. PATENT DOCUMENTS

| 5,168,049 A | 12/1992 | Meade et al. |
| 5,767,379 A | 6/1998 | Baszczynski et al. |
| 6,103,493 A | 8/2000 | Skerra et al. |

FOREIGN PATENT DOCUMENTS

| CA | 2232841-AA | 3/1997 |
| EP | 0835934 A2 | 4/1998 |
| EP | 1132400 A1 | 9/2001 |
| JP | 7-289264 A | 11/1995 |
| JP | 2000-175698 A | 6/2000 |
| JP | 2000-083675 A | 9/2000 |
| WO | WO-86/02077 A1 | 4/1986 |
| WO | WO-89/03422 A | 4/1989 |
| WO | WO-94/00992 A1 | 1/1994 |
| WO | WO-94/11511 A1 | 5/1994 |
| WO | WO-95/04754 A1 | 2/1995 |
| WO | WO-96/40949 A1 | 12/1996 |
| WO | WO-97/07244 A1 | 2/1997 |
| WO | WO-97/11186 A1 | 3/1997 |
| WO | WO-00/14242 A1 | 3/2000 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Database WPI; Section Ch, Week 200022; Derwent Publications Ltd., XP002280661.
Terras et al., The Plant Cell, vol. 7, pp. 573-588 (May 1995).
Nishizawa et al., Theor. Appl. Genet., vol. 99, pp. 383-390 (1999).
Alexander et al., Proc. Natl. Acad. Sci. USA, vol. 99, pp. 7327-7331 (Aug. 1993).
Wu et al., The Plant Cell, vol. 7, pp. 1357-1368 (Sep. 1995).
Hain et al., Nature, vol. 361, pp. 153-156 (Jan. 1993).
Gope et al., Nucleic Acids Research, vol. 15, No. 8, pp. 3595-3606 (1987).
Keinänen et al., Eur. J. Biochem., vol. 220, p. 615-621 (1994).
Gitlin et al., Biochem. J., vol. 256, pp. 279-282 (1988).
Gitlin et al., Biochem. J., vol. 269, pp. 527-530 (1990).
Hofmann et al., Proc. Natl. Acad. Sci., USA, vol. 77, No. 8, pp. 4666-4668 (Aug. 1980).
Freitag et al., Protein Science, vol. 6, p. 1157-1166 (1997).
Schlumbaum et al., Nature, vol. 324, pp. 365-367 (Nov. 1986).
Mauch et al., Plant Physiol., vol. 88, pp. 936-942 (1988).
Oita et al., Biosci. Biotech. Biochem., vol. 60, No. 3, pp. 481-483 (1996).
Terras et al., The Journal of Biological Chemistry, vol. 267, No. 22, pp. 15301-15309 (1992).
Broglie et al., Science, vol. 254, pp. 1194-1197 (Nov. 1991).
Bayer et al, Biochimica et Biophysica Acta, vol. 1263, pp. 60-66 (1995).
Argarana et al, Nucleic Acids Research, vol. 14, No. 4, pp. 1871-1882 (1986).
N. Subramanian, et al., "A Monoclonal Antibody to Avidin Dissociates Quaternary Structure and Curtails Biotin Binding to Avidin and Streptavidin," Archives of Biochemistry and Biophysics, vol. 344, No. 2, pp. 281-288, XP009091219 (1997).

* cited by examiner

*Primary Examiner*—Jennifer E Graser
(74) *Attorney, Agent, or Firm*—Birch, Stewart, Kolasch & Birch, LLP

(57) ABSTRACT

An object of the present invention is to search and identify novel antifungal proteins capable of inhibiting the growth of plant pathogenic microorganisms including *Magnaporthe grisea* and *Rhizoctonia solani* causing two major rice diseases at relatively low concentrations, and further to clone a gene for said protein. The present invention provides an antifungal protein which can be obtained from fraction(s) precipitated by ammonium sulfate precipitation using an aqueous extract from *Pleurotus cornucopiae*, wherein said protein has an antifungal activity against at least rice blast, and exhibits existence of a component having a molecular weight of about 15 kDa as determined by SDS-PAGE method; a gene encoding said protein and uses thereof.

11 Claims, 9 Drawing Sheets

PROTEIN, A GENE ENCODING THEREFOR AND A METHOD OF USING THE SAME

This application is a Divisional of co-pending application Ser. No. 10/471,422 filed on Sep. 11, 2003, and for which priority is claimed under 35 U.S.C. §120, which is the National Stage of PCT/JP02/02295 filed on Mar. 12, 2002, which claims the benefit of priority of Japanese Application No. 2001/68894 filed on Mar. 12, 2001 under 35 U.S.C. §119; the entire contents of all are hereby incorporated by reference.

FIELD OF THE INVENTION

The present invention relates to a novel protein having an antifungal activity and a method for producing thereof, a gene encoding the protein, and a method of using the protein and gene. Specifically, it relates to a protein originated from *Pleurotus cornucopiae* having an antifungal activity against at least rice blast (*Magnaporthe grisea*), a gene encoding the protein, and a method of using the protein and gene.

The present application claims priority based on Japanese Patent Application No. 2001-68894 filed on Mar. 12, 2001, the entire contents of which are incorporated herein as a reference.

BACKGROUND ART

Lytic enzymes such as chitinase and β-1,3-glucanase are known as plant proteins having an antifungal activity against plant pathogenic microorganisms. In vitro experiments have shown that these enzymes can exert the effect if employed alone (Schlumbaum et al. (1986), Nature 324, pp. 365-367), but enhanced effect can generally be obtained if a combination of two or more of such enzymes is used (Mauch et al. (1988), Plant Physiol. 88, pp 936-942). It is known that the growth inhibition concentration of these lytic enzymes against filamentous fungi should be typically about several tens to several hundreds of μg/ml when used alone, or about several μg/ml per enzyme when used in combination. However, none of these lytic enzymes has been reported to have an antifungal effect against rice blast (*Magnaporthe grisea*), which causes extensive damage to rice crops.

Antifungal peptides (AFP) of low-molecular weight such as defensin also have an antimicrobial activity. Among them, Ca-AMP1 (Japanese Domestic Announcement No. 505048/96), CB-1 (Oita et al. (1996), Biosci. Biotech. Biochem. 60, pp. 481-483), R5-AFP1 and R5-AFP2 (Terras et al. 1992, J. Biol. Chem. 267, pp. 15301-15309), and Ace-AMP1 (Japanese Domestic Announcement No. 501424/97) have been reported to have an antifungal effect against rice blast. These low-molecular weight peptides inhibit 50% of the growth of various plant pathogenic microorganisms including the one mentioned above at a concentration in the order of several μg/ml.

Attempts have also been made to create a disease-resistant plant by isolating the gene for a lytic enzyme or a low-molecular weight antifungal peptide and transfecting it into a plant (Broglie et al. (1991), Science 254, pp. 1194-1197; Terras et al. (1995), The Plant Cell 7, pp. 573-588). A recent study of rice reported that transformant rice obtained by over-expressing rice-derived chitinase exerted increased rice blast resistance (Nishizawa et al. (1999) Theor. Appl. Genet. 99:383-390).

Other pathogenic microorganism-resistant plants created by gene introduction have also been reported such as for PR protein (Alexander et al. (1993) Proc. Natl. Acad. Sci. USA 90: pp. 7327-7331), glucose oxidase (Wu et al. (1995) Plant Cell 7: pp. 1357-1368), stilbene synthase (Hain et al. (1993) Nature 361: pp. 153-156), etc.

However, many existing cases fail to obtain transgenic plants having practically acceptable resistance. This may be attributed to the low expression level of the transgenes, and more essentially the low antifungal activity of the antifungal proteins so far reported. Therefore, it would be desirable to identify and practically apply a more potent antifungal protein than conventional ones.

DISCLOSURE OF THE INVENTION

An object of the present invention is to search and identify a novel antifungal protein capable of inhibiting the growth of various plant pathogenic microorganisms, including rice blast (*Magnaporthe grisea*), which causes extensive damage to rice crops.

Another object of the present invention is to clone a gene encoding said novel protein, and to determine the nucleotide sequence thereof.

Still another object of the present invention is to introduce the gene of the present invention into a host organism (microorganism, animal, plant, etc.) to create a transformant, and thereby put to practical use the gene of the present invention.

Still another object of the present invention is to provide an antifungal agent containing the antifungal protein of the present invention.

DETAILED DESCRIPTION OF THE INVENTION

Figure 1:
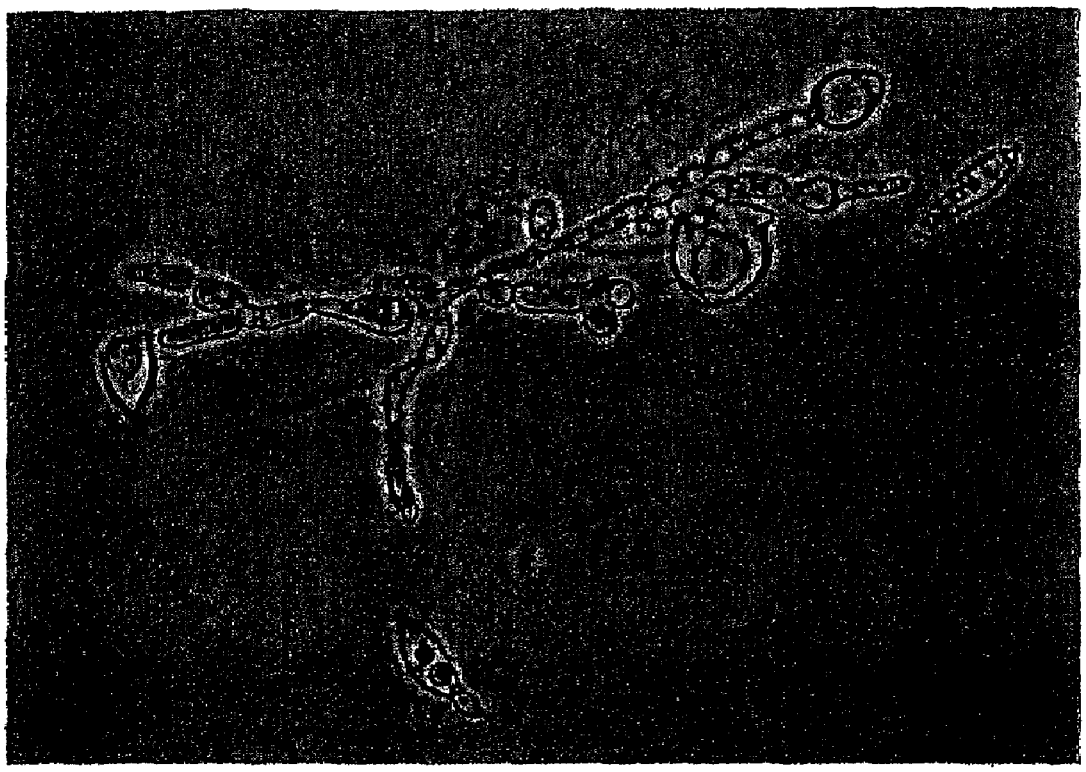
FIG. 1 shows appearance of the growth inhibition of *M. grisea* by the antifungal protein of the present invention (48-hour cultures in the presence of a protein fraction heated at 80° C. for 10 minutes).

With the purpose of solving the problems described above, the present inventors first established an assay system for evaluating an in vitro antifungal activity against rice blast.

Then, protein fractions were extracted from an edible mushroom *Pleurotus cornucopiae* and subjected to the antifungal assay to identify antifungal protein fractions and isolate and purify an antifungal protein by combining ion exchange chromatography and gel filtration. Partial amino acid sequences of the purified protein were determined, on the basis of which oligo DNA sequences were synthesized, and then a partial length cDNA encoding the protein was obtained by RT-PCR. Then, a cDNA library of *Pleurotus cornucopiae* fruit body was screened by using the partial length cDNA as a probe to identify a full-length cDNA encoding the protein, and the total nucleotide sequence thereof was determined. Thus, the total amino acid sequence of the *Pleurotus cornucopiae* antifungal protein and the nucleotide sequence of a gene encoding thereof were identified, thereby completing the present invention.

Accordingly, a first aspect of the present invention provides an antifungal protein which can be obtained from fraction(s) precipitated by ammonium sulfate precipitation method using an aqueous extract from *Pleurotus cornucopiae*, wherein said protein has an antifungal activity against at least rice blast, and exhibits existence of a component having a molecular weight of about 15 kDa as determined by SDS-PAGE method.

The antifungal protein of the present invention is typically characterized by the sequence of 143 amino acids shown in SEQ ID NO: 2 in the Sequence Listing attached hereto. This protein comprises a unit of a polypeptide having a molecular weight of about 15 kDa as estimated by SDS-PAGE (corresponding to a polypeptide consisting of amino acids 8-143 in the sequence of SEQ ID NO: 2 in the Sequence Listing). This protein was also identified as a protein characterized by a molecular weight of about 30 kDa as determined by gel filtration column.

The antifungal protein of the present invention also includes a protein having 141 amino acids shown in SEQ ID NO: 4 in the Sequence Listing. The protein having the amino acid sequence of SEQ ID NO: 4 also comprises a unit of a polypeptide having a molecular weight of about 15 kDa as estimated by SDS-PAGE and has a molecular weight of about 30 kDa as determined by gel filtration column, similar to the protein having the amino acid sequence of SEQ ID NO: 2.

The antifungal protein of the present invention includes antifungal proteins having not only the amino acid sequence of SEQ ID NO: 2 or 4, but also an amino acid sequence containing one or more amino acid modifications compared with the original sequence or an amino acid sequence having a homology of 52% or more to the original sequence and showing an antifungal activity against rice blast.

The antifungal protein of the present invention preferably has an amino acid sequence having a homology of 52% or more, more preferably 60% or more, still more preferably 70% or more, further more preferably 80% or more, especially 90% or more, most preferably 95% or more to the amino acid sequence of SEQ ID NO: 2 or 4 in the Sequence Listing.

The definition of the "protein having a homology of 52% or more" to each specific amino acid sequence as referred to the antifungal protein of the present invention means that it may have a homology of at least 52%, preferably 60% or more, more preferably 70% or more, still more preferably 80% or more, especially 90% or more, most preferably 95% or more.

A second aspect of the present invention provides an antifungal protein comprising either one or a combination of a polypeptide consisting of a partial amino acid sequence of SEQ ID NO: 2 or 4 in the Sequence Listing, e.g. a polypeptide consisting of a partial amino acid sequence 8-143 of SEQ ID NO: 2 or a partial amino acid sequence 8-141 of SEQ ID NO: 4; and a polypeptide having an amino acid sequence containing one or more amino acid changes in any one of said amino acid sequences or a polypeptide having a homology of 52% or more to any one of said amino acid sequences and showing an antifungal activity against rice blast.

A third aspect of the present invention provides a method for producing the antifungal protein of the present invention, which comprises:

collecting fraction(s) from aqueous extract from *Pleurotus cornucopiae*, precipitated by ammonium sulfate precipitation method using 75% saturated ammonium sulfate; and applying said fraction(s) to an ion-exchange column chromatography to collect fraction(s) eluted by NaCl at a concentration between 50 mM-600 mM NaCl.

A fourth aspect of the present invention provides a gene encoding the antifungal protein of the present invention.

The gene of the present invention typically has a nucleotide sequence consisting of bases 71-502 of SEQ ID NO: 1 or a nucleotide sequence of bases 226-651 of SEQ ID NO: 3 (hereinafter sometimes simply referred to as "the nucleotide sequence of SEQ ID NO: 1 or 3"), or a nucleotide sequence containing a substitution, deletion, insertion and/or addition of one or more bases in said nucleotide sequence, or a nucleotide sequence hybridizing to said nucleotide sequence in stringent conditions.

The gene of the present invention generally has a nucleotide sequence preferably having a homology of 60% or more, more preferably 70% or more, still more preferably 80% or more, especially 90% or more, most preferably 95% or more to the nucleotide sequence of bases 71-502 of SEQ ID NO: 1 or the nucleotide sequence of bases 226-651 of SEQ ID NO: 3.

A fifth aspect of the present invention provides an oligonucleotide for obtaining an antifungal protein from *Pleurotus cornucopiae*, produced by a method, which comprises:

selecting two regions from a base sequence of a gene encoding the antifungal protein of SEQ ID NO:1 based on the following requirements;

1) length of each regions is 15-30 bases;
2) proportion of G+C content in a base sequence of each region is 40-60%;

preparing a single-stranded DNA having a base sequence which is identical to said region or complementary to said region, or preparing mixture of single-stranded DNAs based on degeneracy of the genetic code without changing a sequence of amino acid residues encoded by said single-stranded DNAs; and optionally preparing a modified version of said single-stranded DNAs, said modification not altering a binding specificity of the single-stranded DNAs to the base sequence of the gene encoding said antifungal protein.

The oligonucleotide of the present invention preferably has the nucleotide sequence of any one of SEQ ID NOs: 10 to 17 in the Sequence Listing.

A sixth aspect of the present invention provides a method for isolating the gene of the present invention, which comprises performing a nucleic acid amplification reaction using two kinds of oligonucleotides described above as a pair of primers and cDNA library of *Pleurotus cornucopiae* fruit body as a template to amplify a portion of the gene encoding the antifungal protein of the present invention, and screening said cDNA library by using thus obtained amplification product as a probe to isolate the full-length cDNA clone.

A seventh aspect of the present invention provides a recombinant vector comprising the gene of the present invention.

As for the recombinant vector of the present invention, the vector is preferably an expression vector.

An eighth aspect of the present invention provides a transformant obtained by introducing the recombinant vector of the present invention into a host organism.

A ninth aspect of the present invention provides an antifungal agent comprising the antifungal protein of the present invention as an active ingredient.

Preferred Embodiments of the Invention

Preferred embodiments are described in detail below to explain the present invention.

Antifungal Protein Derived from *Pleurotus cornucopiae*

According to a first aspect of the present invention, a protein derived from *Pleurotus cornucopiae* having an antifungal effect against plant pathogenic microorganism is provided. The protein of the present invention is not limited to any specific origin or preparation process so far as it has characteristics defined herein that is, the antifungal protein of the present invention may be naturally occurring or expressed from recombinant DNA by genetic engineering techniques or chemically synthesized.

The protein of the present invention typically has the sequence of 143 amino acids shown in SEQ ID NO: 2 or the sequence of 141 amino acids shown in SEQ ID NO: 4 in the Sequence Listing. However, it is well known that natural proteins include variant proteins having one or more amino acid modifications resulting from differences in varieties of the organisms producing the protein, or the gene mutation depending on differences in ecotypes or the presence of closely similar isozymes. As used herein, the term "amino acid modification" means substitution, deletion, insertion and/or addition of one or more amino acids. The present invention includes the protein having the amino acid sequences shown in SEQ ID NO: 2 or 4 presumed from the nucleotide sequences of the cloned genes, but it is not restricted thereto. Namely, it is intended to encompass all homologous proteins having characteristics defined herein. The homology is at least 52% or more, more preferably 60% or more, still more preferably 70% or more, further more preferably 80% or more, especially 90% or more, most preferably 95% or more.

Generally, a modified protein containing a substitute from one to another amino acid having similar properties (such as a substitute from a hydrophobic amino acid to another hydrophobic amino acid, a substitute from a hydrophilic amino acid to another hydrophilic amino acid, a substitute from an acidic amino acid to another acidic amino acid or a substitutee from a basic amino acid to another basic amino acid) often has similar properties to those of the original protein. Methods for preparing such a recombinant protein having a desired modification using genetic engineering techniques are well known to those skilled in the art and such modified proteins are also included in the scope of the present invention. For example, site-specific mutagenesis described in Molecular Cloning, 2nd edition (Sambrook et al., (1989)) can be used.

As used herein, the percent homology can be determined by comparison with sequence information using the BLAST program described by Altschul et al. (Nucl. Acids. Res. 25, pp. 3389-3402, 1997), for example. This program is available from the website of National Center for Biotechnology Information (NCBI) or DNA Data Bank of Japan (DDBJ) on the Internet. Various conditions (parameters) for homology searches with the BLAST program are described in detail on the site, and searches are normally performed with default values though some settings may be somewhat changed. Alternatively, it can be determined by comparison with sequence information using a genetic sequence analysis software program such as GENETYX (Software Development Co., Ltd.) or DNASIS (Hitachi Software Engineering).

Homology searches were performed through GenBank databases using BLAST for the *Pleurotus cornucopiae*-derived antifungal protein of the present invention, and the gene thereof as well as their homologs and proteins having an amino acid sequence encoded thereby. Database searches for the amino acid sequence of the first *Pleurotus cornucopiae*-derived antifungal protein of the present invention (total amino acid sequence of SEQ ID NO: 2) revealed matches to streptavidin v2 of *Streptomyces* violaceus (Accession No: Q53533, Bayer et al. (1995) Biochim Biophys Acta 1263: pp. 60-66), streptavidin v1 (Accession No: □53532), streptavidin of *Streptomyces* avidin ii (Accession No.: P22629, Argarana et al. (1986) Nucleic Acids Res 14: pp. 1871-1882), etc. The homology of these three sequences extends over 128 amino acids, and was 50%, 49% and 49%, respectively. A homology of 51.7% to a core streptavidin mutant w79f (Chain B) (Freitag et al. (1997) Protein Sci. 6: pp. 1157-1166) was also shown over 120 amino acids.

Egg white avidin (Gope et al. (1987) Nucleic Acids Res 15: pp. 3595-3606) and several avidin-related proteins (Keinanen et al. (1994) Eur J Biochem 220: pp. 615-621) were also matched at lower homology degrees. These facts indicate that the present protein is a novel protein.

Database searches of the amino acid sequence of the second *Pleurotus cornucopiae*-derived antifungal protein of the present invention (total amino acid sequence of SEQ ID NO: 4) showed homology of 50%, 48% and 48% to streptavidin v2, v1 and streptavidin, respectively.

The present antifungal protein was named "tamavidin" because it was a novel streptavidin-like protein purified from an edible mushroom *Pleurotus cornucopiae* (Tamogitake). Here, the gene derived from the purified protein is called tam1, the protein having an amino acid sequence encoded thereby is called tamavidin 1, a homolog of tam1 is called tam 2, and the protein having an amino acid sequence encoded thereby is called tamavidin 2.

The amino acid residues 1-7 of SEQ ID NOs: 2 and 4 are thought to correspond to the leader peptide of a precursor of the antifungal protein. Thus, the amino acid residues 8-143 of SEQ ID NO: 2 and 8-141 of SEQ ID NO: 4 are matured forms of the antifungal protein. Accordingly, the present invention also provides an antifungal protein comprising either one or a combination of a polypeptide consisting of a partial amino acid sequence of SEQ ID NO: 2, that is amino acids 8-143, or a partial amino acid sequence of SEQ ID NO: 4, that is amino acids 8-141; and a polypeptide having an amino acid sequence containing one or more amino acid modifications in any one of said amino acid sequences or a polypeptide having a homology higher than 51% to any one of said amino acid sequences and showing an antifungal activity against rice blast.

Purification and isolation of the protein of the present invention can be accomplished by appropriately combining conventional methods for purification and isolation of proteins, such as ammonium sulfate precipitation, ion exchange chromatography (Mono Q, Q Sepharose or DEAE), gel filtration (Superose 6, Superose 12).

For example, ground powder of *Pleurotus cornucopiae* is extracted with a buffer, and then filtered, and the supernatant is allowed to stand with ammonium sulfate at a suitable concentration, e.g. 75% saturation to give precipitates, as described in the examples below. The precipitates are dialyzed and then eluted by ion exchange chromatography using a gradient of salt concentration (e.g., 50 mM-600 mM NaCl), and then fractions containing a desired protein are recovered on the basis of an antifungal activity. Fractions having a molecular weight of around 30 kDa can be recovered by gel filtration. The antifungal protein of the present invention has a molecular weight of, but is not limited to, about 15 kDa as determined by SDS-PAGE.

Alternatively, said protein can be obtained in mass quantity by introducing a DNA sequence consisting of 71 (or 92) to 502 of the DNA sequence of SEQ ID NO: 1 or a DNA sequence consisting of 226 (or 247) to 651 of the DNA sequence of SEQ ID NO: 3 into *E. coli*, yeasts or insects or certain animal cells by known introduction techniques using an expression vector capable of amplifying in each host and expressing it.

The amino acid sequence of this protein and the DNA sequence encoding it disclosed herein can be wholly or partially used to readily isolate a gene encoding a protein having a similar physiological activity from other species, preferably fungi, more preferably Eumycota including mushrooms, molds and yeasts, and Basidiomycotina including many mushrooms, more preferably mushrooms of Agaricales to which *Pleurotus cornucopiae* belongs, e.g. *Pleurotus ostreatus, Lentinus edodes, Armillariella mellea, Tricholoma matsutake, shimeji* mushrooms, *Flammulina velutipes, Grifola frondosa, Cantharellus cibarius, Pleurotus eryngii* using basic genetic engineering techniques including hybridization and PCR. In such cases, these novel proteins are also included in the scope of the present invention.

Gene for the Antifungal Protein

The present invention also provides a gene encoding the antifungal protein of the present invention. The type of the gene of the present invention is not specifically limited, but may be any of native DNA, recombinant DNA or chemically synthesized DNA, and any genomic DNA clone or cDNA clone.

The gene of the present invention typically has the nucleotide sequence shown in SEQ ID NO: 1 or 3. However, the nucleotide sequence of a clone obtained in the examples shown below is only one example. It is well-known to those skilled in the art that natural genes include variations resulting from differences in varieties of the organisms producing the gene, or from minor mutation depending on differences in ecotypes or from minor mutation depending on the presence of closely similar isozymes. Accordingly, the gene of the present invention is not limited to only that having the nucleotide sequence of SEQ ID NO: 1 or 3 in the Sequence Listing, and is intended to encompass all genes encoding the antifungal protein of the present invention.

Especially, the amino acid sequence of the proteins and the DNA sequence encoding thereof disclosed herein can be wholly or partially used to readily isolate from other species a gene encoding a protein having a similar physiological activity using genetic engineering techniques, including hybridization and nucleic acid amplification reactions. In such cases, these genes are also included in the scope of the present invention.

BLAST searches through GenBank databases using the DNA sequence of a gene encoding the *Pleurotus cornucopiae*-derived antifungal protein (DNA sequence of 71-502 of SEQ ID NO: 1) and the DNA sequence of a gene encoding the second *Pleurotus cornucopiae*-derived antifungal protein (DNA sequence 226-651 of SEQ ID NO: 3) found only several sequences showing homology in a very short range (23 bp) but not the DNA sequence of streptavidin. This means that the DNA sequence encoding the novel protein of the present invention is not highly homologous to the DNA sequence of streptavidin on the DNA level.

More specifically, a genetic sequence analysis software program GENETYX-WIN ver 3.2 (Software Development Co., Ltd.) was used to analyze homology of the total amino acid sequences of the *Pleurotus cornucopiae* antifungal proteins of the present invention (tamavidins 1 and 2) to streptavidin (which differs from streptavidins v2 and v1 by only 9 amino acids and 1 amino acid, respectively). As a result, the amino acid sequence of tamavidin 1 encoded by tam1 of the present invention showed a homology (amino acid identity) of 46.7% and the amino acid sequence of tamavidin 2 encoded by tam2 showed 48.1%. The homology of the total DNA sequence (SEQ ID NOs: 1 and 3 in the Sequence Listing) to streptavidin was 53.8% for tam1 and 51.0% for tam2. The homology of the *Pleurotus cornucopiae* antifungal protein encoded by tam1 to egg white avidin was 31.2% in amino acid sequence and 42.4% in DNA sequence, and the homology of the *Pleurotus cornucopiae* antifungal protein encoded by tam 2 to egg white avidin was 36.2% in amino acid sequence and 41.8% in DNA sequence. The homology between the amino acid sequences of tamavidin 1 and tamavidin 2 and the homology between the DNA sequences of the genes tam1 and tam 2 encoding them were 65.5% and 64.5%, respectively.

As compared with streptavidin, tamavidin 1 and tamavidin 2 of the present invention are truncated by the N terminal 33 amino acids, but all the tryptophan (W) residues (Gitlin et al. (1988) Biochem. J. 256: pp. 279-282) and tyrosine (Y) residues (Gitlin et al. (1990) Biochem. J. 269: pp. 527-530) possibly involved in binding to biotin are conserved, (Y 34 and 45 and W 82, 98 and 110 in the amino acid sequence of SEQ ID NO: 2, Y 34 and 45 and W 80, 96 and 108 in the amino acid sequence of SEQ ID NO: 4).

The average molecular weights of the regions presumed to be mature protein regions (stretches 8-143 of the amino acid sequence of SEQ ID NO: 2, and 8-141 of the amino acid sequence of SEQ ID NO: 4) were calculated at 15158.4 and 14732.2, respectively, close to the average molecular weights of mature streptavidin and mature avidin (16490.6 and 14342.9, respectively).

Streptavidin is derived from *Actinomyces Streptomyces avidinii* and avidin is derived from birds (*Gallus gallus*) egg white. Proteins closely similar to streptavidin so far isolated include streptavidins v1 and v2 from *Streptomyces violaceus* (Bayer et al. (1995) Biochim Biophys Acta 1263: pp. 60-66), and homologs of the avidin gene so far isolated include an avidin-related gene from avian (avr1-avr5, Keinanen et al. (1994) Eur J Biochem 220: pp. 615-621). Streptavidins v1 and v2 differ from streptavidin in amino acid sequence by 1 amino acid and 9 amino acids, respectively, and the avidin-related protein has a homology to avidin of 68-78% in amino acid sequence and 88-92% in DNA sequence. The homology between streptavidin and avidin is 29.2% in amino acid sequence, and 46.8% in DNA sequence.

Preferred examples of the antifungal protein of the present invention, tamavidins 1 and 2 are derived from a species of the Basidiomycetes, *Pleurotus cornucopiae*, and have a homology of 46.7% and 48.1%, respectively, to streptavidin in amino acid sequence and a homology of 31.2% and 36.2%, respectively, to avidin in amino acid sequence, as described above. Thus, tamavidins 1, 2 form a third group distinct from the streptavidin group of *Actinomyces* and the avian avidin group. Such avidin-like protein was first isolated from sources other than actinomycetes and avian. Tamavidins 1, 2 are avidin-like proteins present in mushrooms, and other varieties of mushrooms are likely to contain similar proteins. The amino acid sequences of tamavidins 1, 2 and the DNA sequences of tam1, tam2 can be used to further search and isolate such proteins and genes thereof.

Hybridization conditions used for screening homologous genes are not specifically limited, but stringent conditions are generally preferred, such as several hours to overnight in 5×SSC, 5×Denhardt's solution, 1% SDS at 25-68° C. as described in Current Protocols in Molecular Biology Vol. 1 (John Wiley and Sons, Inc.) or Molecular Cloning 2nd edition (Sambrook et al. (1989)). The hybridization temperature here is more preferably 45-68° C. (without formamide) or 30-42° C. (50% formamide). Washing conditions involve e.g. 0.2× SSC at 45-68° C. It is well known to those skilled in the art that a DNA containing a nucleotide sequence having homology higher than a predetermined level can be cloned by appropriately selecting hybridization conditions such as formamide level, salt level and temperature, and all of the homologous genes thus cloned are included in the scope of the present invention.

Nucleic acid amplification reactions here include reactions involving temperature cycles such as polymerase chain reaction (PCR) (Saiki et al., 1985, Science, 230, pp. 1350-1354), ligase chain reaction (LCR) (Wu et al., 1989, Genomics, 4, pp. 560-569; Barringer et al., 1990, Gene, 89, pp. 117-122; Barany et al., 1991, Proc. Natl. Acad. Sci. USA, 88, 189-193) and transcription-based amplification (Kwoh et al., 1989, Proc. Natl. Acad. Sci. USA, 86, pp. 1173-1177) as well as isothermal reactions such as strand displacement amplification (SDA) (Walker et al., 1992, Proc. Natl. Acad. Sci. USA, 89, pp. 392-396; Walker et al., 1992, Nuc. Acids Res., 20, pp. 1691-1696), self-sustained sequence replication (3SR) (Guatelli et. al., 1990, Proc. Natl. Acad. Sci. USA, 87, pp. 1874-1878), and Qβ replicase system (Lizardi et al., 1988, Bio-Technology, 6, pp. 1197-1202). Other reactions such as nucleic acid sequence-based amplification (NASBA) using competitive amplification of a target nucleic acid and a mutant sequence disclosed in European Patent No. 0525882 can also be used. A PCR is preferred.

Homologous genes cloned by hybridization or nucleic acid amplification reactions as above preferably have a homology of 60% or more, more preferably 70% or more, still more preferably 80% or more, especially 90% or more, most preferably 95% or more to the nucleotide sequence shown in SEQ ID NO: 1 in the Sequence Listing.

Oligonucleotide

According to the present invention, an oligonucleotide for obtaining an antifungal protein derived from *Pleurotus cornucopiae* is also provided, which is produced by a method comprising:

selecting two regions from a base sequence of a gene encoding the antifungal protein of SEQ ID NO:1 based on the following requirements;

1) length of each region is 15-30 bases;
2) proportion of G+C content in a base sequence of each region is 40-60%;

preparing a single-stranded DNA having a base sequence which is identical to said region or complementary to said region, or preparing mixture of single-stranded DNAs based on degeneracy of the genetic code without changing a sequence of amino acid residues encoded by said single-stranded DNAs; and optionally preparing a modified version of said single-stranded DNAs, said modification not altering a binding specificity of the single-stranded DNAs to the base sequence of the gene encoding said antifungal protein. The oligonucleotide of the present invention can be used for e.g. hybridization or amplification reactions such as PCR using suitable two of the oligonucleotides as a primer pair for detecting or isolating the gene of the present invention.

The oligonucleotide of the present invention preferably has a nucleotide sequence shown in any one of SEQ ID NOs: 10-19 in the Sequence Listing. The nucleotide sequences of SEQ ID NOs: 10-13 were designed on the basis of the amino acid sequence of SEQ ID NO: 9 as PCR primers for cloning a gene fragment encoding a part of the protein and comprise all the bases capable of encoding the amino acid. The nucleotides of SEQ ID NOs: 14-17 are primers synthesized for primer walking for decoding the total nucleotide sequences of tam1 and tam2 genes. The nucleotides of SEQ ID NOs: 18-19 are PCR primers prepared on the basis of SEQ ID NO: 3 for amplifying the total ORF to construct an expression vector for expressing recombinant tamavidin 2 protein having the amino acid sequence of SEQ ID NO: 4.

A partial fragment of the gene of the present invention can be isolated by nucleic acid amplification reactions such as PCR using a cDNA library of *Pleurotus cornucopiae* fruit body as a template with an appropriate pair of the above oligonucleotides. A full-length cDNA clone can be isolated by screening the cDNA library with an amplification product thus obtained as a probe by e.g. plaque hybridization. The procedures and conditions for nucleic acid amplification reactions and the plaque hybridization conditions are well-known to those skilled in the art.

For example, hybridization conditions of rather low stringency may be used, such as, but not limited to, room temperature and washing at higher salt concentrations such as 2×SSC at 37° C. as described in Current Protocols in Molecular Biology Vol. 1 (John Wiley and Sons, Inc.) or Molecular Cloning (Sambrook et al., supra.).

Preparation of Recombinant Antifungal Proteins

The protein of the present invention has a very strong antifungal activity. For example, it completely inhibits the germination of spores of rice blast (*M. grisea*) at a concentration as low as 50 ng/ml (see Example 4 below). No germination of spores appears at this concentration even after extended incubation, suggesting that the effect of the protein of the present invention against rice blast may be a fungus-killing effect rather than partial inhibition of growth. To our knowledge, no antifungal proteins that can completely inhibit the growth of pathogenic microorganism at such a low concentration (on the order of nanograms) have been reported thus far. In the examples below, a major rice pathogen, rice blast, was used as a plant pathogen for the antifungal assay for purifying an antifungal protein, but it is highly possible that the *Pleurotus cornucopiae* antifungal proteins identified herein have comparable antifungal effects against other plant pathogenic damage such as *Rhizoctonia solani*.

Thus, the *Pleurotus cornucopiae*-derived antifungal protein of the present invention has a potent antifungal activity, so that it can be used in formulations such as antifungal agents and pesticides, which can contain the antifungal protein in an active form. In this case, the present protein is purified from *Pleurotus cornucopiae* by using e.g. an ion exchange column or a gel filtration column as described in the examples below. However, the *Pleurotus cornucopiae* antifungal protein of the present invention can be prepared more conveniently in mass quantity by introducing and expressing DNA having the nucleotide sequence of 71-502 of SEQ ID NO: 1 or 226-651 of SEQ ID NO: 3 encoding the protein in *E. coli*, yeasts, insects or animal cells using an expression vector capable of amplifying in each host (Example 5).

The present invention also provides a recombinant vector containing the gene of the present invention. Methods for inserting a DNA fragment of the gene of the present invention into a vector such as a plasmid are described in e.g. Sambrook, J. et al, Molecular Cloning, A Laboratory Manual (2nd edition), Cold Spring Harbor Laboratory, 1.53 (1989). Commercially available ligation kits (e.g. available from TAKARA SHUZO CO., LTD.) can be conveniently used. Thus obtained recombinant vectors (e.g. recombinant plasmids) are introduced into host cells (e.g., E-coil TB1, LE392 or XL-1Blue).

Suitable methods for introducing a plasmid into a host cell include the use of calcium phosphate or calcium chloride/rubidium chloride, electroporation, electroinjection, chemical treatment with PEG or the like, the use of a gene gun described in Sambrook, J. et al., Molecular Cloning, A Laboratory Manual (2nd edition), Cold Spring Harbor Laboratory, 1.74 (1989).

Vectors can be conveniently prepared by linking a desired gene by a standard method to a recombination vector available in the art (e.g. plasmid DNA). Specific examples of suitable vectors include, but are not limited to, *E. coli*-derived plasmids such as pBluescript, pUC18, pUC19, pBR322, pTrc99A.

Expression vectors are especially useful for the purpose of producing a desired protein. The types of expression vectors are not specifically limited so far as they can express a desired gene in various prokaryotic and/or eukaryotic host cells to produce a desired protein, but preferably include expression vectors for *E. coli* such as pQE-30, pQE-60, pMAL-C2, pMAL-p2, pSE420; expression vectors for yeasts such as pYES2 (genus *Saccharomyces*), pPIC3.5K, pPIC9K, pAO815 (all genus *Pichia*); and expression vectors for insects such as pBacPAK8/9, pBK283, pVL1392, pBlueBac4.5.

Transformants can be prepared by introducing a desired expression vector into a host cell. Suitable host cells are not specifically limited so far as they are compatible with expression vectors and transformable, and include various cells such as natural cells or artificially established recombinant cells commonly used in the field of the present invention. Examples are bacteria (*Escherichia, Bacillus*), yeasts (*Saccharomyces, Pichia*), animal cells, insect cells, plant cells, etc.

Host cells are preferably *E. coli*, yeasts or insect cells, specifically *E. coli* such as M15, JM109, BL21; yeasts such as INVSc1 (genus *Saccharomyces*), GS115, KM71 (all genus *Pichia*); insect cells such as BmN4, silkworm larvae. Examples of animal cells are those derived from mouse, *Xenopus*, rat, hamster, simian or human or culture cell lines established from these cells. Plant cells include those derived from tobacco, *Arabidopsis*, rice, maize, wheat, etc., but are not specifically limited so far as they can be cultured.

When a bacterium, especially *E. coli* is used as a host cell, the expression vector generally consists of at least a promoter/operator region, an initiation codon, a gene encoding a desired antifungal protein, a termination codon, a terminator and a replicable unit.

When a yeast, plant cell, animal cell or insect cell is used as a host cell, the expression vector generally preferably contains at least a promoter, an initiation codon, a gene encoding a desired antifungal protein, a termination codon and a terminator. It may also contain a DNA encoding a signal peptide, an enhancer sequence, non-translated 5' and 3' regions of the desired gene, a selectable marker or a replicable unit, etc., if desired.

A preferred initiation codon in vectors of the present invention is a methionine codon (ATG). Termination codons may be conventional termination codons (for example, TAG, TGA, TAA).

The replicable unit means a DNA capable of replicating the entire DNA sequence in a host cell, and includes natural plasmids, artificially modified plasmids (plasmids prepared from natural plasmids) and synthetic plasmids, etc. Preferred plasmids are pQE30, pET or PCAL or their artificial modifications (DNA fragments obtained by treating pQE30, pET or PCAL with suitable restriction endonucleases) for *E. coli*; pYES2 or pPIC9K for yeasts; and pBacPAK8/9 for insect cells.

Enhancer sequences and terminator sequences may be those commonly used by those skilled in the art such as those derived from SV40.

As for selectable markers, those commonly used can be used by standard methods. Examples are genes, which provide resistance to antibiotics such as tetracycline, ampicillin, kanamycin, neomycin, hygromycin or spectinomycin.

Expression vectors can be prepared by consecutively and cyclically linking at least the above-described promoter, initiation codon, gene encoding a desired antifungal protein, termination codon and terminator region to a suitable replicable unit. In this process, a suitable DNA fragment (such as a linker or another restriction enzyme site) can be used by standard methods such as digestion with a restriction enzyme or ligation with T4DNA ligase, if desired.

Introduction [transformation (transduction)] of expression vectors of the present invention into host cells can be conducted by using known techniques.

For example, bacteria (such as *E. coli, Bacillus subtilis*) can be transformed by the method of Cohen et al. [Proc. Natl. Acad. Sci. USA, 69, 2110 (1972)], the protoplast method [Mol. Gen. Genet., 168, 111 (1979)] or the competent method [J. Mol. Biol., 56, 209 (1971)]; *Saccharomyces cerevisiae* can be transformed by the method of Hinnen et al [Proc. Natl. Acad. Sci. USA, 75, 1927 (1978)] or the lithium method [J. Bacteriol., 153, 163 (1983)]; plant cells can be transformed by the leaf disc method [Science, 227, 129 (1985)] or electroporation [Nature, 319, 791 (1986)]; animal cells can be transformed by the method of Graham [Virology, 52, 456 (1973)]; and insect cells can be transformed by the method of Summers et al. [Mol. Cell. Biol., 3, 2156-2165 (1983)].

Plant transforming vectors are especially useful for the purpose of creating a disease-resistant plant using a DNA fragment of the present invention. The types of vectors for plants are not specifically limited so far as they can express the gene of interest in plant cells to produce the protein, but preferably include pBI221, pBI121 (Clontech), and vectors derived there from. Especially, examples of vectors for transforming monocotyledons include pIG121Hm and pTOK233 (Hiei et al., Plant J., 6, 271-282 (1994)), and pSB424 (Komari et al., Plant J., 10, 165-174 (1996)).

Transgenic plants can be prepared by replacing the β-glucuronidase (GUS) gene in the above vectors with a DNA fragment of the present invention to construct a plant-transforming vector and introducing it into a plant. The plant-transforming vector preferably contains at least a promoter, an initiation codon, a desired gene (a DNA sequence of the present invention or a part thereof), a termination codon and a terminator. It may also contain a DNA encoding a signal peptide, an enhancer sequence, non-translated 5' and 3' regions of the desired gene, a selectable marker region, etc., if desired.

Promoters and terminators are not specifically limited so far as they are functional in plant cells, among which constitutive expression promoters include the 35S promoter initially being inserted in the above vectors as well as promoters for actin and ubiquitin genes. However, an inducible promoter may be more preferably inserted. This allows transgenic plants to be resistant to a pest by producing the protein only when they come into contact with it. Suitable inducible promoters include promoters of genes of phenylalanine ammonia-lyase, chitinase, glucanase, thionine, and osmosin and other promoters of genes responding to pests or stresses.

Methods for the gene transduction into a plant include the use of *Agrobacterium* (Horsch et al., Science, 227, 129 (1985); Hiei et al., Plant J., 6, pp. 271-282 (1994)), electroporation (Fromm et al., Nature, 319, 791 (1986)), PEG (Paszkowski et al., EMBO J., 3, 2717 (1984)), microinjection (Crossway et al., Mol. Gen. Genet., 202, 179 (1986)), particle bombardment (McCabe et al., Bio/Technology, 6, 923 (1988)), but are not specifically limited so far as they are suitable for transfecting a gene into a desired plant. The species of host plants are not specifically limited, either, so far as they are compatible with the plant transforming vectors of the present invention and transformable, specifically plants commonly used in the field of the present invention, e.g. dicotyledons such as tobacco, *Arabidopsis*, tomato, cucumber, carrot, soybean, potato, beet, turnip, Chinese cabbage, rape, cotton and petunia; and monocotyledons such as rice, corn and wheat.

The protein of the present invention can be expressed (produced) by culturing transformed cells containing an expression vector prepared as described above in a nutrient medium. The nutrient medium preferably contains a carbon, inorganic nitrogen or organic nitrogen source necessary for the growth of host cells (transformants). Examples of carbon sources include e.g. glucose, dextran, soluble starch, sucrose and methanol. Examples of inorganic or organic nitrogen sources include ammonium salts, nitrates, amino acids, corn steep liquor, peptone, casein, beef extract, soybean meal and potato extract. If desired, other nutrients (e.g. inorganic salts such as sodium chloride, calcium chloride, sodium dihydrogen phosphate and magnesium chloride; vitamins; antibiotics such as tetracycline, neomycin, ampicillin and kanamycin) may be contained.

Incubation takes place by techniques known in the art. Incubation conditions such as temperature, the pH of the medium and the incubation period are appropriately selected to produce the protein of the present invention in mass quantity. For expression in *E. coli*, incubation conditions for expressing a recombinant protein include, but are not limited to, incubation at a temperature of 4-40° C. and induction with 0.01-5.0 mM IPTG.

The protein of the present invention can be obtained from the cultures as follows. When the protein of the present invention accumulates in host cells, the host cells are collected by centrifugation or filtration or the like and suspended in a suitable buffer (e.g. a buffer such as about 10 M-100 mM Tris buffer, phosphate buffer, HEPES buffer or MES buffer at a pH depending on the buffer used, but desirably in the range of pH 5.0-9.0), then the cells are disrupted by a method suitable for the host cells used and centrifuged to collect the contents of the host cells. When the protein of the present invention is secreted outside host cells, the host cells and the culture medium are separated by centrifugation or filtration or the like to give a culture filtrate. The host cell lysates or the culture filtrates can be used to isolate/purify the protein of the present invention directly or after ammonium sulfate precipitation and dialysis.

An isolation/purification method is as follows. When the protein of interest is tagged with 6× histidine, GST, maltose-binding protein or the like, conventional methods based on affinity chromatography suitable for each tag can be used. As a non-limiting example, a recombinant antifungal protein tagged with 6× histidine at the N-terminus was expressed in Example 4 below. This recombinant protein was purified using Ni-NTA agarose (Qiagen) having affinity for 6× histidine. When the protein of the present invention is produced without using these tags, the method described in detail in the examples below based on ion exchange chromatography can be used, for example. These methods may be combined with gel filtration or hydrophobic chromatography, isoelectric chromatography or the like. Purification on an iminobiotin affinity column can also be applied as described by Hofmann et al., (Proc. Natl. Acad. Sci. USA, 77: pp. 4666-4668 (1980)). In Example 5 below, the recombinant protein, tamavidin 2 was obtained at a yield of 1 mg from 50 mL of *E. coli* cultures.

The antifungal proteins of the present invention obtained by genetic engineering techniques or purified from natural sources as described above have antifungal activity. The antifungal activity can be determined by, but not limited to, incubating microtiter plates containing spores of rice blast suspended in a culture medium (e.g. ½ PD, sucrose-peptone) in the presence of the antifungal protein of the present invention at a predetermined concentration, e.g. 10 ng/ml-1000 ng/ml, preferably 50 ng/ml at 28° C. for 48 hours, and evaluating whether or not the growth/proliferation of rice blast (e.g. extension of hyphae) is inhibited as compared with a control not containing the antifungal protein (Example 4).

Alternatively, the following assay can also be applied. A colony of rice blast is placed at the center of an agar medium prepared in a Petri dish and a predetermined amount of an aqueous solution of the antifungal protein of the present invention is dropped around the colony, and the Petri dish is incubated at 28° C. for about 48 hours to a week. Then, the antifungal activity can be assayed by evaluating whether or not the extension of hyphae of rice blast in regions treated with the antifungal protein is inhibited as compared with untreated regions.

Antifungal Agents

The proteins of the present invention have a potent antifungal activity. For example, it inhibits the growth of hyphae of rice blast at a low concentration such as 50 ng/ml in our antifungal assay. In the examples below, *M. grisea* and *Rhizoctonia solani*, which cause extensive damage to rice crops, were used as plant pathogens for the antifungal assay. The *Pleurotus cornucopiae* antifungal protein identified herein showed an antifungal effect against them. The protein of the present invention is most likely to have an antifungal effect against plant pathogenic microorganisms other than *M. grisea*.

Thus, the *Pleurotus cornucopiae*-derived antifungal protein of the present invention has a potent antifungal activity, so that it can be used in formulations such as antifungal agents and pesticides, which can contain the antifungal protein in an active form. In this case, the protein of the present invention can be prepared in mass quantity by inserting a DNA sequence encoding the protein of the present invention into an expression vector functional in e.g. *E. coli* or yeasts as described above.

The antifungal protein of the present invention is a novel streptavidin-like protein, suggesting that it bind to one of vitamins, biotin (vitamin H). Rice blast is known to require biotin for its growth. These facts suggest that the present antifungal protein binds to free biotin present in assay media to induce biotin deficiency in the media, with the result that the growth of rice blast was inhibited. In fact, the antifungal activity of tamavidin 1 of the present invention was abolished when biotin was excessively added into the assay medium as described in Example 4 below. We further found that commercially available streptavidin and avidin also have an antifungal effect against rice blast similar to tamavidin 1, and demonstrated that this effect is also abolished by biotin.

The present invention suggested the possibility that resistance to disease, especially to rice blast can be conferred on plants by controlling the amount of one of vitamins, biotin. The possibility that disease-resistance can be conferred by controlling a vitamin has not been so far known. This is a novel concept. This concept is also included in the present invention. For example, a formulation containing the antifungal protein of the present invention as an active ingredient can be used as a pesticide. In this case, biotin-binding proteins other than the antifungal protein of the present invention (e.g. streptavidin of *Streptomyces avidinii* and egg white avidin, and homologs thereof) are also included in the same concept.

Thus, the present invention provides an antifungal agent containing the antifungal protein of the present invention as an active ingredient. Normally, the antifungal agent of the present invention can be systemically or locally applied to plants.

Dispersion dose of the antifungal agent depends on the type of plant, growth stage, condition, dispersion method, treating time, the type of the protein applied (e.g. a full-length protein or a protein obtained by substitution, deletion, insertion and/or addition of a part of the former protein), the weather and the soil of the site where the plant grows, and other factors, and the antifungal agent can be dispersed once or more daily or at intervals of several days. The antifungal agent of the present invention can also be dispersed in admixture with solubilizers, suspending agents, emulsifiers, etc., if necessary. Aqueous or non-aueous solubilizers and suspending agents are mixed as at least one inert diluent with one or more active substances. Examples of aqueous diluents include distilled water and saline. Examples of non-aqueous diluents include propylene glycol, polyethylene glycol, and vegetable oils such as olive oil and alcohols such as ethanol.

Such antifungal compositions may further contain auxiliary agents such as preservatives, humectants, emulsifiers, dispersants or stabilizers (e.g. arginine, aspartic acid, etc.).

These compositions are sterilized by filtration through a bacteriostatic filer or the addition of a bactericide or irradiation, if necessary. They can also be prepared as sterile solid compositions by, for example, freeze-drying and then dissolved in distilled water or other solvents before use.

The dosage form of the antifungal agent thus obtained may be appropriately determined depending on the purpose, i.e. it can be applied in the form of tablets, pills, dusts, granules, solutions, emulsions, etc. in admixture with the additives mentioned above.

Disease-resistant plants can also be created by inserting a gene encoding the antifungal protein of the present invention into a plant. Thus, a disease-resistant plant can be created by e.g. introducing a plant with a construct in which a promoter functional in the plant is linked to a gene encoding the antifungal protein of the present invention and a terminator functional in the plant is further added downstream. In this case, a DNA sequence encoding a signal peptide for extracellular secretion functional in the plant may be added to the 5' side of the gene encoding the antifungal protein of the present invention in order to promote the secretion of tamavidin outside plant cells. Alternatively, the codon usage of the gene can be adapted for monocotyledons or dicotyledons without affecting the amino acids to promote accumulation of the antifungal protein inside or outside plant cells. Methods for creating disease-resistant plants using combinations of these means are also included in the present invention.

Applications of tamavidin, avidin, streptavidin or closely similar proteins thereto for creating disease-resistant plants and to plants other than rice are also included in the present invention. Although the pathogenic fungus analyzed herein is rice blast, it is quite possible that other plant pathogenic fungi and pathogenic bacteria requiring biotin for their growth are also covered.

Moreover, similar effects may naturally be produced against not only plant pathogenic microorganisms but also animal pathogenic fungi essentially requiring biotin for their growth, especially pathogenic microorganisms to human and domestic animals, and therefore, the present invention encompasses the uses of the antifungal protein of the present invention, avidin or streptavidin, and closely similar proteins thereto as therapeutic agents in such scenes.

The DNA sequence of streptavidin has already been disclosed (Garwin et al., WO/8602077), but the DNA sequences of tam1 and tam2 of the present invention were not matched to the DNA of streptavidin during ordinary database searches and actually showed homology to the DNA of streptavidin at only 51.0-53.8% during forced comparison using a nucleic acid/amino acid sequence analysis software program, as described above.

Streptavidin and avidin have already been widely used as experimental reagents in various scenes in molecular biology, biochemistry or the like because they have very strong binding affinity to biotin and derivatives thereof. For example, they are used in detection systems of nucleic acids and proteins (Liang. WO/9707244) or purification methods based on the binding affinity to biotin of streptavidin or avidin expressed as a fusion protein (Skerra et al. EP835934, Kopetzki. WO/9711186). Tamavidin 1 and tamavidin 2 of the present invention can also be used in these applications currently widely known or reported.

Plant-related applications of streptavidin or avidin so far reported include the creation of male sterile plants using avidin (Howard and Albertsen. WO/9640949), the application of streptavidin or avidin as insecticidal protein (Czapla et al. WO/9400992), and the production of avidin in plants (Baszczynski et al. U.S. Pat. No. 5,767,379). The uses of streptavidin or avidin described in these documents can also apply to the *Pleurotus cornucopiae*-derived antifungal protein of the present invention.

REFERENCES

1. Schlumbaum et al. (1986) Nature 324: pp. 365-367
2. Mauch et al. (1988) Plant Physiol. 88: pp. 936-942
3. Japanese Domestic announcement No. 505048/96
4. Oita et al. (1996) Biosci. Biotech. Biochem. 60: pp. 481-483
5. Terras et al. (1992) J. Biol. Chem. 267: pp. 15301-15309
6. Japanese Domestic announcement No. 501424/97
7. Broglie et al. (1991) Science 254: pp. 1194-1197
8. Terras et al. (1995) The Plant Cell 7: pp. 573-588
9. Nishizawa et al. (1999) Theor Appl Genet. 99:383-390
10. Alexander et al. (1993) Proc. Natl. Acad. Sci. USA 90: pp. 7327-7331
11. Wu et al. (1995) Plant Cell 7: pp. 1357-1368
12. Hain et al. (1993) Nature 361: pp. 153-156
13. Bayer et al. (1995) Biochim Biophys Acta 1263: pp. 60-66
14. Argarana et al. (1986) Nucleic Acids Res 14: pp. 1871-1882
15. Freitag et al. (1997) Protein Sci. 6: pp. 1157-1166
16. Gope et al. (1987) Nucleic Acids Res 15: pp. 3595-3606
17. Keinanen et al. (1994) Eur J Biochem 220: pp. 615-621
18. Gitlin et al. (1988) Biochem. J 256: pp. 279-282
19. Gitlin et al. (1990) Biochem J 269: pp. 527-530
20. Hofmann et al., Proc. Natl. Acad. Sci. USA, 77: pp. 4666-4668 (1980)
21. Garwin et al. WO/8602077
22. Liang. WO/9707244
23. Skerra et al. EP835934
24. Kopetzki. WO/9711186
25. Howard and Albertsen. WO/9640949
26. Czapla et al. WO/9400992
27. Baszczynski et al. U.S. Pat. No. 5,767,379.

The following examples further illustrate the present invention without, however, limiting the invention thereto.

EXAMPLES

Example 1

Construction of an Assay System

1) Establishment of an Assay System

Cultivation of pathogenic fungi: *Magnaporthe grisea* (rice blast) (race 337, strain TUS-1 obtained from National Agricultural Research Center for Tohoku Region of the Ministry of Agriculture, Forestry and Fisheries of Japan) was cultured on an oatmeal medium (Difco, supplemented with 1% sucrose) to give conidia for use as an inoculum. The spores were stored at −80° C. in 10% glycerol, if necessary.

*Rhizoctonia solani* (strain JT872) was cultured on ½ potato dextrose broth (PD, Difco) for 2 days, and three mycelia of about 5 mm were gently ground in ½ PD in a Teflon homogenizer to give hyphal fragments for use as an inoculum.

These inocula were added to 96-well microtiter plates (Corning) at a density of about 1,000 conidia of *M. grisea* per well or about 300 hyphal fragments of *R. solani* per well in 100 µl of ½ PD and incubated in an incubator at 28° C. for 48 hours. The growth of the fungi was monitored by measuring the absorbance at 595 nm with a microplate reader (Benchmark, Bio-Rad).

2) Extraction of Protein from *Pleurotus cornucopiae*

After 100 g of commercially available fruit bodies of *Pleurotus cornucopiae* were finely cut with scissors in advance, they were frozen in liquid nitrogen and ground in a mortar into fine powder, and then extracted with 300 ml of 100 mM HEPES-KOH buffer, pH 7.5 at 4° C. for 30 minutes with gentle stirring. The extract was filtered through Miracloth and then centrifuged at 10,000×g for 20 minutes. Then, the supernatant was allowed to stand at 4° C. overnight with 75% saturation ammonium sulfate. Then, precipitates were obtained by centrifugation at 15,000×g for 20 minutes and dissolved in 3 ml of 10 mM HEPES-KOH buffer, pH 7.5 and dialyzed against 20 mM HEPES-KOH buffer, pH 7.5 using a dialysis tube (Spectra/Por1 MWCO 6-8000, Spectrum Medical Industries). Insolubles were removed by centrifugation to give a *Pleurotus cornucopia* protein sample. The protein level of the *Pleurotus cornucopia* protein sample was determined by the Bradford method using bovine serum albumin (BSA) as a standard protein.

Example 2

Purification of Antifungal Protein

1) Antifungal Activity of the Crude *Pleurotus cornucopiae* Protein Sample

The culture systems of *M. grisea* and *R. solani* were added with a given amount the crude *P. cornucopiae* protein sample added immediately after starting cultivation, incubated for 2 days (46-48 hours), and then evaluated for an antifungal activity by measuring the absorbance. The results showed that the *Pleurotus cornucopiae* extract contained a substance having a high antifungal activity against both *Magnaporthe grisea* and *Rhizoctonia solani*. Complete inhibition of germination and inhibition of the growth of hyphae were observed against *M. grisea* and inhibition of the growth of hyphae was observed against *R. solani*. As for cells of *M. grisea*, the cytoplasm was separated from the cell wall and looked like plasmolysis.

To further analyze the nature of the antifungal activity detected, residual activity was tested after heating. The antifungal assay was performed after heating at 60 and 80° C. for 10 minutes. The strength of activity was estimated by diluting the protein sample. As a result, the antifungal activity against both *M. grisea* and *R. solani* was comparable before and after heating at 60° C. However, the antifungal activity against *R. solani* disappeared after heating at 80° C. In contrast, a new activity was shown against *M. grisea* by swelling hyphal apices to stop the growth after heating at 80° C., though the activity of inducing plasmolysis was lost (FIG. 1).

To know the approximate molecular weight of the core substance governing these activities contained in heated fractions of the crude *Pleurotus cornucopiae* protein sample, the sample was fractionated through an ultrafiltration membrane to study an antifungal activity by separating the sample into fractions which passed through or not an Ultrafree MC10,000 NMWL filter unit (cut-off molecular weight 10000, Millipore) used as an ultrafiltration membrane. As a result, all the activities existed in only fractions retained on the membrane. Thus, the molecular weight of the active core was estimated to be at least 10000 or higher.

2) Purification by Ion Exchange Chromatography Then, the antifungal protein was purified.

Figure 2:
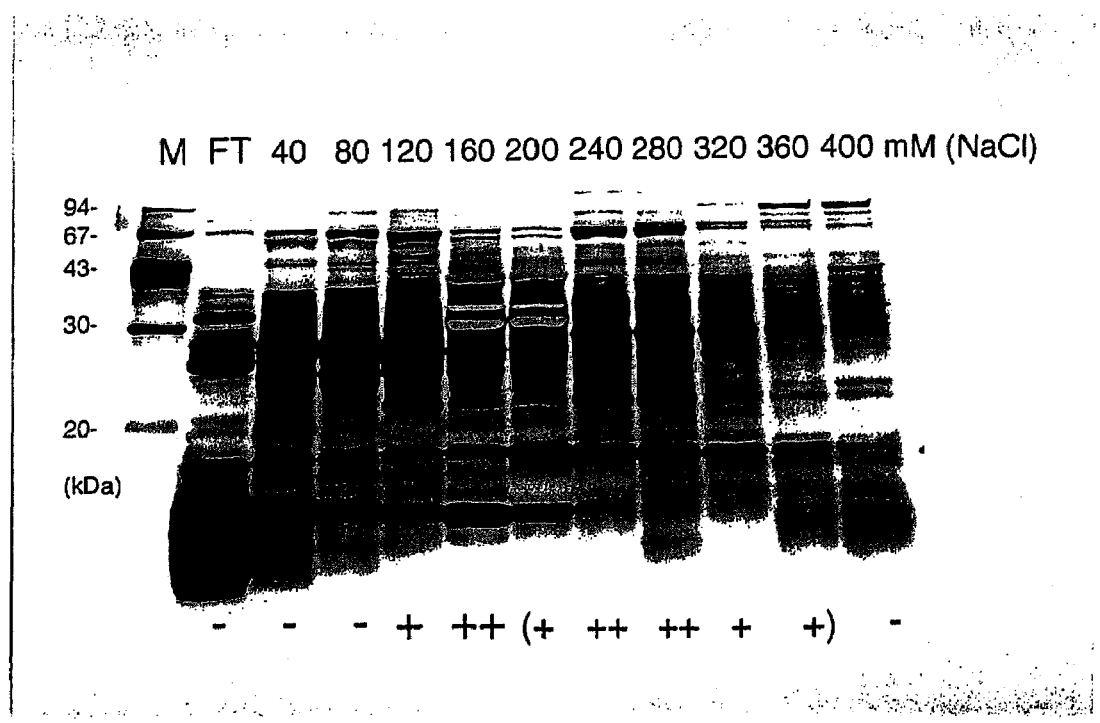
FIG. 2 shows electrophoretic patterns of *Pleurotus cornucopiae* protein fractions separated by a Q-Sepharose FF column in relation to an antifungal activity. M represents a molecular weight marker, and FT represents the fraction having passed through the column. The symbols (−, +, ++) below the lanes indicate the strength of the antifungal activity. The antifungal activities shown in parentheses belong to fractions other than the purified ones described in the present invention.

Initially, 150 mg/20 ml of the crude protein sample was loaded on an home-built column (inner diameter 1.5 cm×height 10 cm, column volume 10 ml) packed with an ion exchanger Q Sepharose FF (Pharmacia) to partially purify the antifungal protein. A buffer of 50 mM Tris pH 8.0, 50 mM NaCl to 50 mM Tris pH 8.0, 600 mM NaCl as elution buffer with a gradient (50 mM to 600 mM NaCl) was used at a flow rate of 2 ml/min over 100 minutes. A part of each fraction (12.5 ml) was subjected to the antifungal assay against *M. grisea* and SDS-PAGE electrophoresis. The protein solution of each fraction was reacted with an equivalent amount of 2×SDS running buffer (Sambrook et al. (1989) Molecular Cloning 2nd edition, Cold Spring Harbor) at 95° C. for 5 minutes, and then run by SDS-PAGE electrophoresis according to the method of Laemmli (Laemmli (1970) Nature 227: pp. 680-685). The gel used is 15% PAGEL (ATTO) and the protein was detected with a Silver Stain II kit Wako (Wako Pure Chemical Industries). To estimate the approximate molecular weight and the amount of the protein, a molecular weight marker was run (LMW marker kit: Pharmacia LKB, sizes 94 kDa, 67 kDa, 43 kDa, 30 kDa, 20.1 kDa, 14.4 kDa). The electrophoretic patterns of protein by silver staining are shown in FIG. 2 in relation to the strength of an antifungal activity.

Two peaks appeared as antifungal activities at NaCl concentrations of 160 mM and 240 mM-280 mM. The protein contained in the peak at 160 mM acted by swelling hyphal apices to stop the growth, and did not disappear after heating at 70° C. for 10 minutes. However, the protein contained in the peat at 240 mM-280 mM induced plasmolysis in *M. grisea* and disappeared after heating at the same temperature. Accordingly, an attempt was made to purify the antifungal protein contained in the peat at 160 mM.

The fractions corresponding to the NaCl concentration of 120 mM-240 mM were transferred to a dialysis tube (Spectra/Porl MWCO 6-8000, Spectrum Medical Industries), and dialyzed against 50 mM Tris-HCl pH 8.0, 50 mM NaCl at 4° C. overnight. Concentration on Centriprep-10 (cut-off molecular weight 10,000, Amicon) was followed by heating at 70° C. for 30 minutes. After centrifugation, the supernatant was filtered through a 0.22 µm filter. This protein sample (about 10 ml) was loaded on MonoQ HR 5/5 (Pharmacia) to separate/purify antifungal protein. A buffer of 50 mM Tris-HCl, pH 8.0, 50 mM NaCl to 50 mM Tris-HCl, pH 8.0, 500 mM NaCl was used as elution buffer with a gradient (50 mM to 500 mM NaCl) at a flow rate of 1 ml/min over 40 minutes starting at 20 minutes after loading the sample. A part of each fraction (1 ml) was subjected to the antifungal assay against *M. grisea* and SDS-PAGE electrophoresis.

Figure 3:
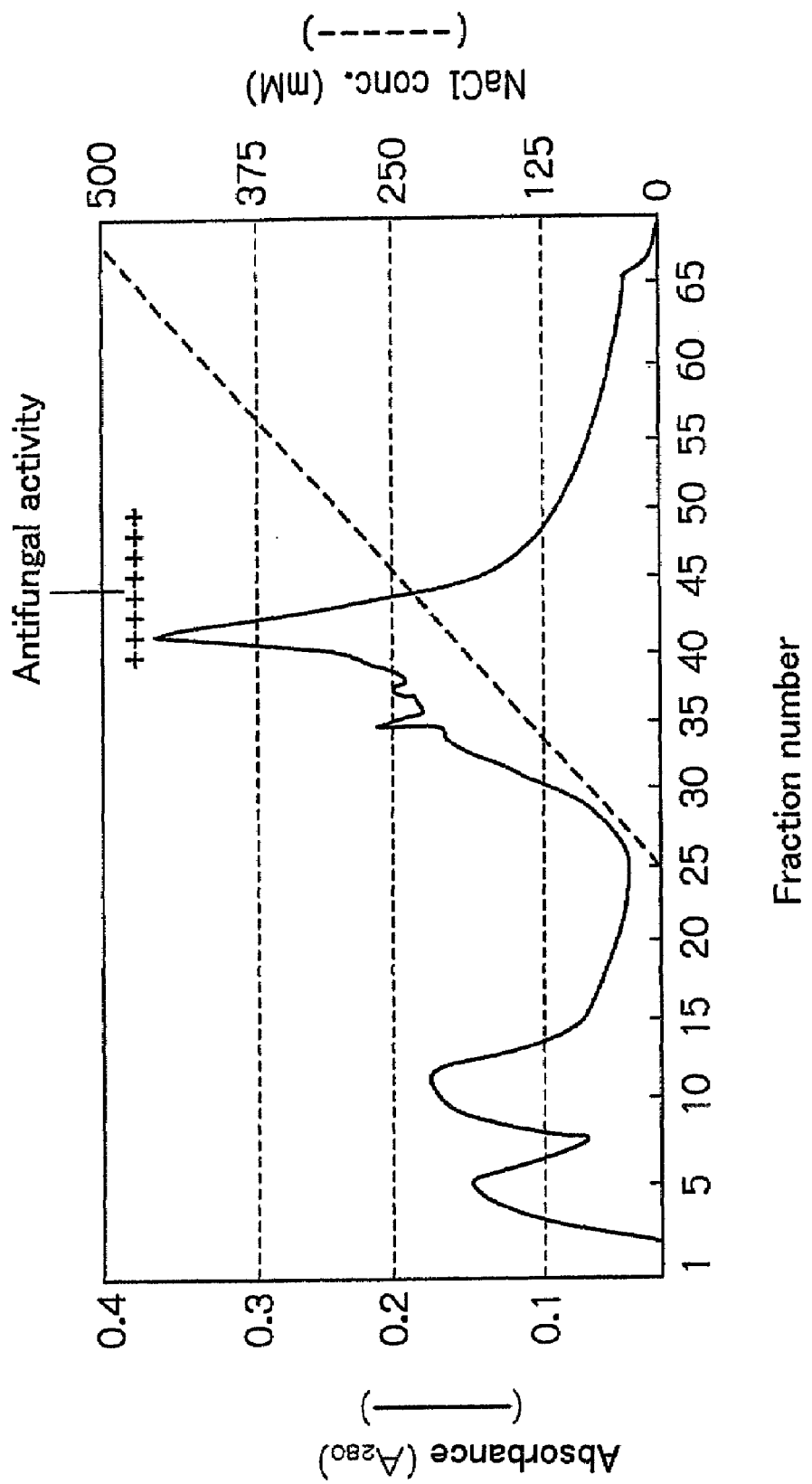
FIG. 3 shows a separation chart of the *Pleurotus cornucopiae* antifungal protein by MonoQ column in relation to an antifungal activity. The elution positions showing the antifungal activity are indicated by +.

The HPLC chart is shown in FIG. 3 in relation to the strength of an antifungal activity. The results show that an elution peak of the antifungal protein appeared around an ionic strength (NaCl concentration) of 200 mM-260 mM.

Figure 4:
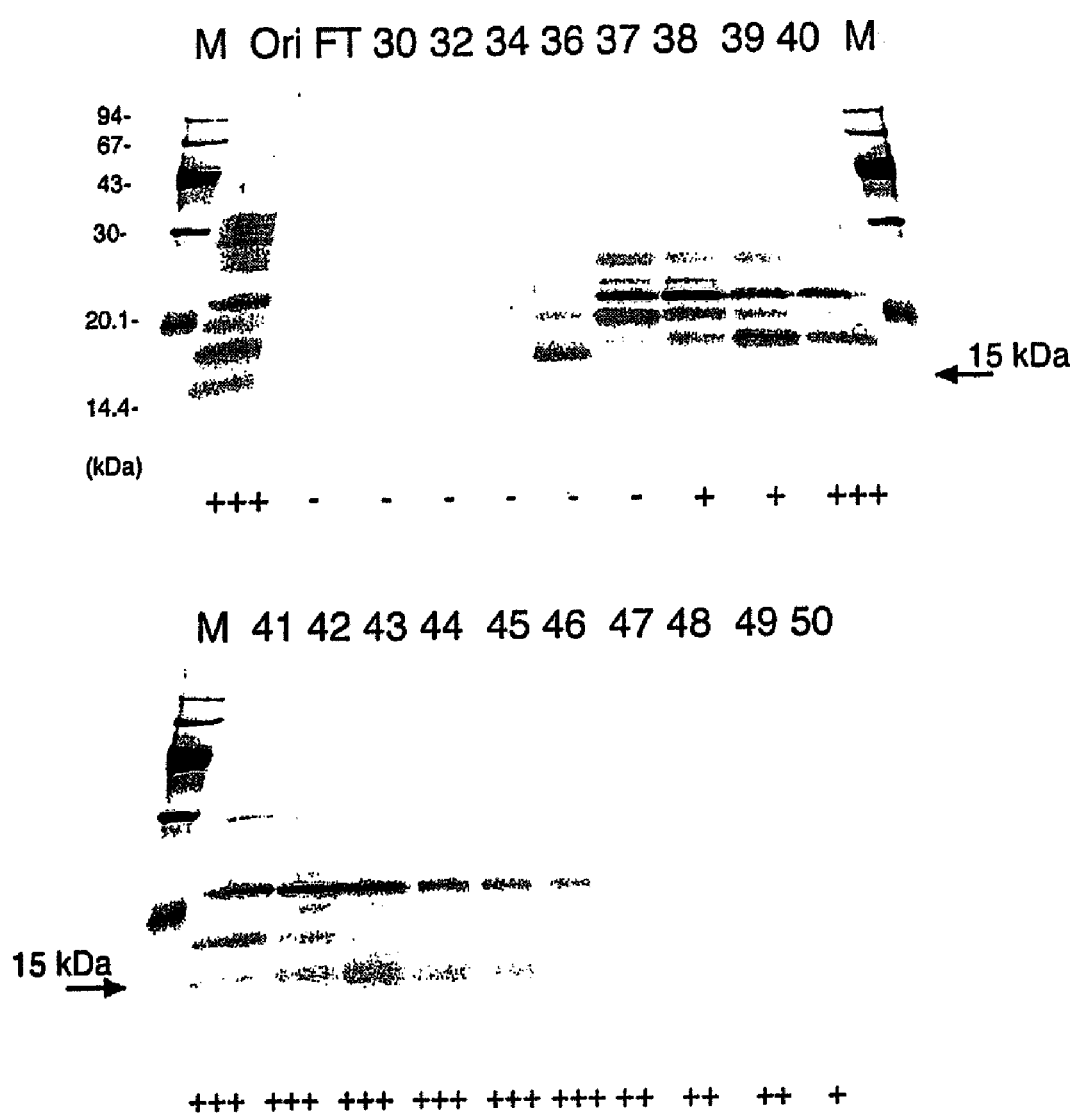
FIG. 4 shows electrophoretic patterns of *Pleurotus cornucopiae* protein separated by a Mono Q column in relation to an antifungal activity. The numbers above the lanes correspond to the fraction numbers in FIG. 3, M represents a molecular weight marker, and Ori represents the Q-Sepharose fraction applied on Mono Q. The symbols (−, +, ++, +++) below the lanes indicate the strength of an antifungal activity. The arrows indicate the antifungal protein (15 kDa).

The electrophoretic pattern is shown in FIG. 4 in relation to the strength of an antifungal activity. The figure at the top of each lane corresponds to the fraction number in FIG. 3. Careful examination of protein bands possibly related to an antifungal activity found two bands of about 15 kD as likely candidates (arrows in FIG. 4). The strength of the bands and the level of an antifungal activity are positively correlated, suggesting the possibility that the bands may be the core antifungal protein.

3) Purification by Gel Filtration and Estimation of the Molecular Weight

To purify *Pleurotus cornucopiae* antifungal protein and estimate the native molecular weight, Mono Q fractions #41-46 obtained as above were concentrated on an Ultrafree MC10,000 NMWL filter unit (Millipore) and loaded on a gel filtration column Superose 6 HR 10/30 (Pharmacia). The buffer used is 50 mM MES-NaOH pH 6.0, 50 mM NaCl at a flow rate of 0.5 ml/min. The molecular weights and the approximate elution times of the protein were predicted by Gel filtration standard (BIO-RAD), and then MonoQ fractions having an antifungal activity were loaded.

Figure 5:
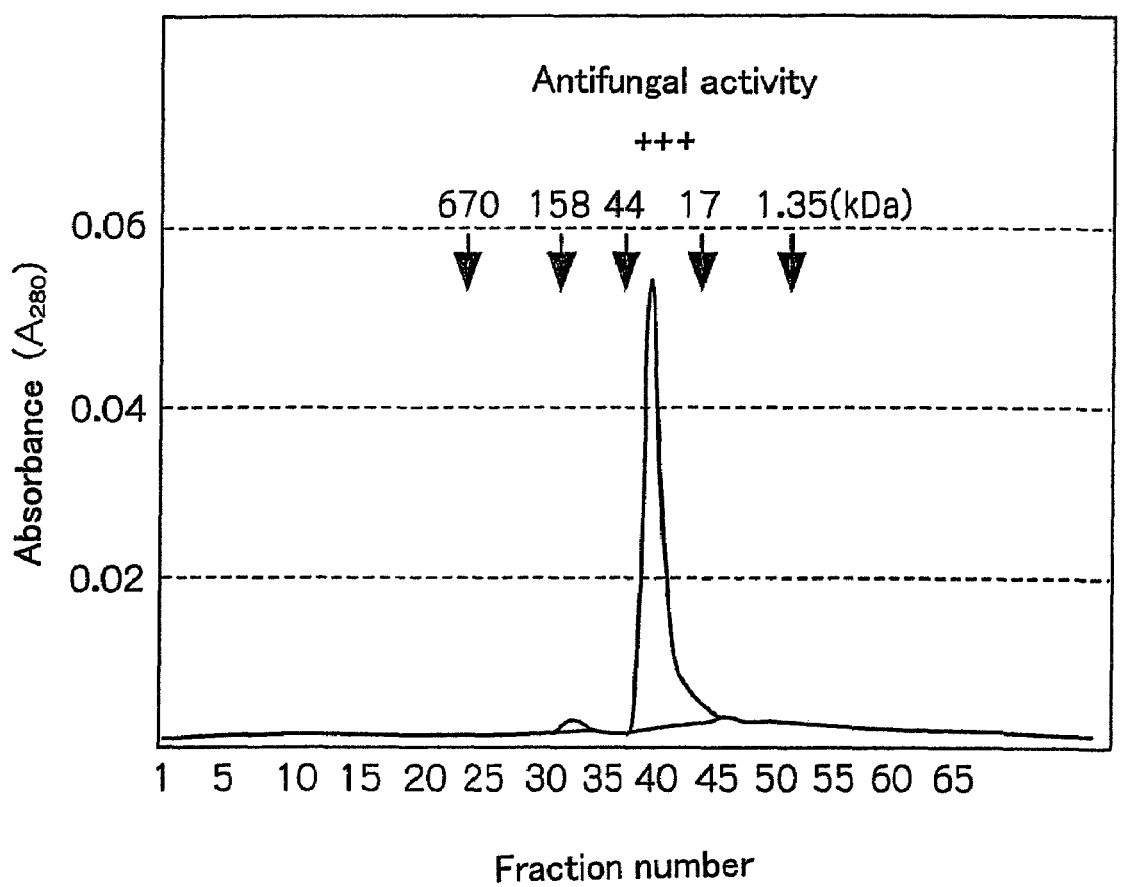
FIG. 5 shows a separation chart of the *Pleurotus cornucopiae* antifungal protein by Superose 6 in relation to an antifungal activity. The arrows indicate the elution positions of Gel filtration standard (BIO-RAD). The positions of fractions showing the antifungal activity are indicated by +.
Figure 6:
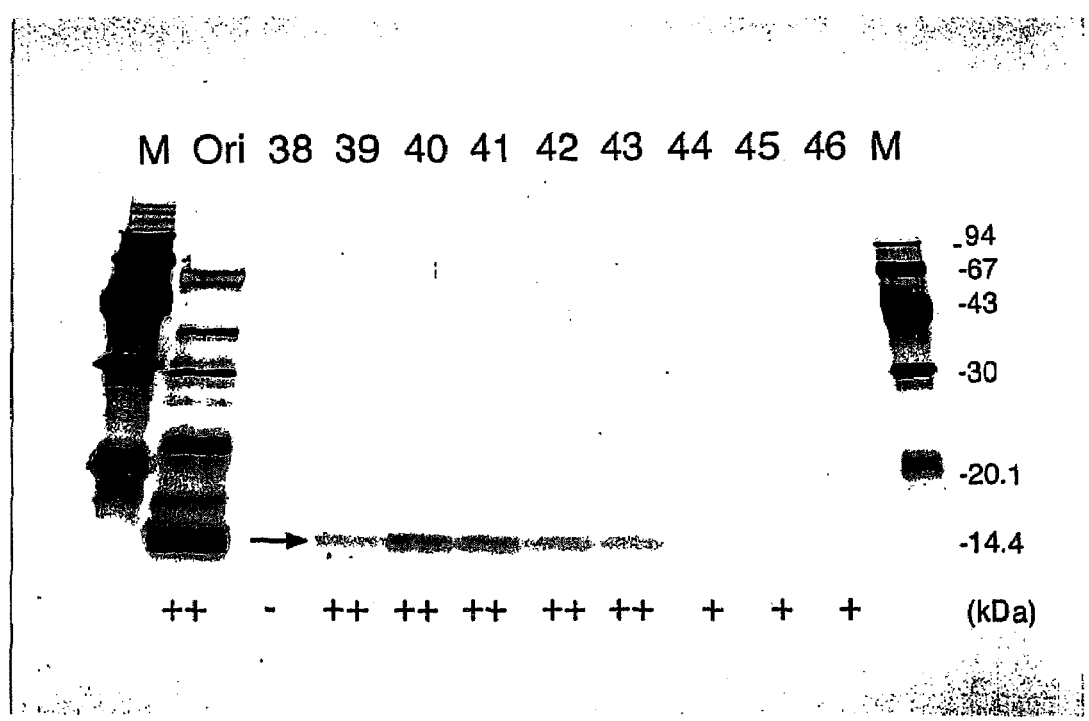
FIG. 6 shows electrophoretic patterns of *Pleurotus cornucopiae* protein purified by Superose 6 in relation to an antifungal activity. The numbers above the lanes correspond to the fraction numbers in FIG. 5, Ori represents the MonoQ fraction applied on Superose 6, and M represents a molecular weight marker. The symbols (−, +, ++) below the lanes indicate the strength of an antifungal activity. The arrow indicates the antifungal protein (15 kDa).

As a result, a sharp peak appeared at 30 kDa when the protein was monitored at A280 (FIG. 5). The Antifungal activity was concentrated at the peak and close to 30 kDa. This shows that the antifungal activity of *Pleurotus cornucopiae* is derived from a single protein having a molecular weight of about 30 kDa as determined by gel filtration. When each fraction (0.25 ml) was silver-stained after SDS-PAGE, a band of 15 kDa shown in FIG. 4 was detected only around 30 kDa (FIG. 6). No band other than 15 kDa appeared, strongly suggesting again that the protein of 15 kDa contributes to an antifungal activity. The amount of the antifungal protein was estimated from a molecular weight marker (trypsin inhibitor at 20.1 kDa) by a densitometer and the 50% growth inhibition concentration against *M. grisea* was calculated at about 50 ng/ml. The amount of the antifungal protein that can be purified from a crude weight of 100 g of *Pleurotus cornucopiae* fruit bodies by the above method was about 0.2 mg.

Example 3

Isolation of cDNA

1) Determination of the Amino Acid Sequence of *Pleurotus cornucopiae* Antifungal Protein The Superose 6 fraction obtained as above was concentrated on an Ultrafree MC 10,000 NMWL (Millipore) and subjected to SDS-PAGE electrophoresis. The fraction was transferred to a PVDF membrane (Millipore) in a buffer system containing neither Tris nor glycine, and lightly stained with Coomassie Brilliant Blue R-250 and then destained. Then, the protein band of 15 kDa possibly contributing to an antifungal activity was excised. The protein of 15 kDa was partially digested with lysyl endopeptidase (Wako Pure Chemical Industries) or V8 protease (Wako Pure Chemical Industries).

As a result, a 14 kDa fraction was obtained by digestion with lysyl endopeptidase and 14 kDa and 12 kDa fractions were obtained by digestion with V8 protease. These bands were also transferred after migration. Then, the N-terminal amino acid sequence was determined by Edman degradation using a gas-phase protein the Sequencer (HPG1005A Protein Sequencing System).

As a result, the following 44 amino acids were determined from the 15 kDa protein:

```
                                            (SEQ ID NO: 5)
N'-Leu Xaa Gly Xaa Trp Tyr Asn Glu Leu Gly Xaa Xaa

Met Asn Leu Thr Ala Asn Lys Asp Gly Ser Leu Xaa

Gly Thr Tyr His Ser Asn Val Gly Glu Val Pro Xaa

Xaa Tyr His Leu Ala Gly Arg Tyr-C'
``` wherein and hereinafter Xaa is unknown. The following 50 amino acids were determined from the lysyl endopeptidase digest of the 14 kDa protein:

```
                                         (SEQ ID NO: 6)
N'-Asp Gly Ser Leu Thr Gly Thr Tyr His Ser Asn Val

Gly Glu Val Pro Pro Thr Tyr His Leu Ser Gly Arg

Tyr Asn Leu Gln Pro Pro Ser Gly Gln Gly Val Thr

Leu Gly Xaa Ala Val Ser Phe Glu Asn Thr Xaa Ala

Asn Val-C'.
```

The following 21 amino acids were determined from the V8 protease digest of the 14 kDa protein:

```
                                         (SEQ ID NO: 7)
N'-Leu Thr Gly Thr Trp Tyr Asn Glu Leu Gly Ser Thr

Met Asn Leu Thr Ala Asn Lys Asp Gly-C'.
```

The following 23 amino acids were determined from the 12 kDa protein:

```
                                         (SEQ ID NO: 8)
N'-Leu Thr Gly Thr Xaa Tyr Asn Glu Leu Gly Ser Thr

Xaa Asn Leu Thr Ala Asn Xaa Asp Gly Xaa Leu-C'.
```

Finally, the following 69 amino acids were determined:

```
                                         (SEQ ID NO: 9)
N'-Leu Thr Gly Thr Trp Tyr Asn Glu Leu Gly Ser Thr

Met Asn Leu Thr Ala Asn Lys Asp Gly Ser Leu Thr

Gly Thr Tyr His Ser Asn Val Gly Glu Val Pro Pro

Thr Tyr His Leu Ser Gly Arg Tyr Asn Leu Gln Pro

Pro Ser Gly Gln Gly Val Thr Leu Gly Xaa Ala Val

Ser Phe Glu Asn Thr Xaa Ala Asn Val-C'.
```

2) Design of Degenerate Primers

Based on the amino acid sequence determined in 1), four primers containing all the possible bases were synthesized. The figures in parentheses show the degree of degeneracy.

```
TMR1:
5'-acnggnacntggtayaayg-3'  (256)       (SEQ ID NO: 10)
(corresponding to the amino acid residues Thr2 to
Glu8 of SEQ ID NO: 9)

TMR2:
5'-garytiggiwsnacntatgaa-3'  (256)     (SEQ ID NO: 11)
(corresponding to the amino acid residues Glu8 to
Asn14 of SEQ ID NO: 9)

TMF1:
5'-gtrttytcraaiswiacn-3'  (128)        (SEQ ID NO: 12)
(corresponding to the amino acid residues Ala59 to
Thr65 of SEQ ID NO: 9)

TMF2:
5'-cciarigtnacnccytgncc-3'  (256)      (SEQ ID NO: 13)
(corresponding to the amino acid residues Gly51 to
Gly57 of SEQ ID NO: 9)
``` wherein "i" means "inosine", "r" means "g or a", "y" means "c or t", "w" means "a or t", "s means "g or c", and "n" means "a or g or c or t", respectively.

3) Construction of a cDNA Library of *Pleurotus cornucopiae* Fruit Body

Total nucleic acid was extracted from *Pleurotus* cornucopiae fruit body by the SDS phenol method and total RNA was recovered by lithium chloride precipitation. Then, *Pleurotus cornucopiae* mRNA was prepared from the total RNA using an mRNA purification kit (Pharmacia). From about 5 g of fruit bodies, 10 μg of mRNA was obtained, of which 5 μg was used in a ZAP cDNA synthesis kit (Stratagene) to synthesize cDNA. About 0.5-5 kb of cDNA was fractionated by gel filtration and ligated to a Uni-ZAP XR vector (Stratagene) and packaged with Gigapack III (Stratagene). All the procedures were carried out as according to instructions in the kit. The titer of thus constructed cDNA library of *Pleurotus cornucopiae* fruit body was estimated at about 3,000,000 pfu.

4) Preparation of Probes by RT-PCR

PCR was performed using the primers synthesized in 2) and the cDNA synthesized in 3) as a template to try to amplify a partial length cDNA of *Pleurotus cornucopiae* antifungal protein suitable as a probe for screening libraries. The reaction conditions were as follows: 50 μl of a reaction solution containing 10 ng of cDNA, 5 μl of 10×Ex taq buffer, 4 μl of 2.5 mM each dNTP, 5 pmoles/sequence of each primer and 1 μl of Ex taq (Takara)+Taq START antibody (Clontech) was run in 1 cycle at 94° C. for 3 min, 35 cycles of at 94° C. for 1 min, 50° C. for 1 min, and 72° C. for 1 min, and then 1 cycle at 72° C. for 6 min using a programmed temperature control system PC-700 (ASTEK). As a result, a product of about 150-190 bp was amplified with each of primer pairs TMR1-TMRF1, TMR1-TMRF2, TMR2-TMRF1 and TMR2-TMRF2.

These PCR products were gel-purified and cloned into a vector pCRII (Invitrogen). These clones were sequenced to reveal that they contained two cDNAs, i.e. a cDNA encoding strictly the same amino acid sequence as determined in 1) (derived from pairs TMR2-TMRF1 and TMR2-TMRF2; especially, the cDNA derived from pair TMR2-TMRF2 is designated as TM100), and a cDNA encoding an amino acid sequence having a homology of about 75% to the amino acid sequence determined in 1) (derived from pairs TMR1-TMRF1, TMR1-TMRF2; especially, the cDNA derived from pair TMR1-TMRF1 is designated as TM75).

5) Screening of the Full-length cDNA

The cDNA clones TM100 and TM75 obtained in 4) were excised from the vector and used as probes to screen the cDNA library of *Pleurotus cornucopiae* fruit body. In a square Petri dish (14×10 cm), about 20,000 pfu of phage was plated with a host XL1-blue MRF' according to instructions given for a ZAP cDNA synthesis kit (Stratagene). The plaque was brought into contact with Hybond-N+ nylon membrane filter (Amersham) to denature DNA by alkali as instructed for the membrane, and immobilized on the membrane. The probes were $^{32}$P-labeled using a rediprime II™ DNA labelling system (Amersham). Hybridization was performed in 0.5 M NaHPO₄ (pH 7.2), 7% SDS, 1 mM EDTA at 65° C. overnight, followed by washing twice in 40 mM NaHPO₄ (pH 7.2), 1% SDS, 1 mM EDTA at 65° C. for 20 minutes. Primary screening from about 160,000 pfu of phage gave 600 positive clones with TM100 probe and 30 positive clones with TM75 probe. Among them, 24 clones from TM100 probe and 12 clones from TM75 probe were further subjected to secondary screening and a third screening also aimed at purifying the plaque, and all the clones selected were in vivo excised as instructed for the ZAP cDNA synthesis kit (Stratagene). As a result, 18 clones from TM100 probe and 12 clones from TM75 probe were recovered as cDNA integrated into the phagemid vector pBluescript SK. The insert length of these clones was identified by restriction endonuclease analysis.

6) Determining the Base Sequences

The total nucleotide sequence of the longest clone of each of the above cDNA clones was determined. Initially, both 5' and 3' nucleotide sequences of the clone were determined using M13 primers (takara) on ABI PRISM Fluorescence Sequencer (Model 310 Genetic Analyzer, Perkin Elmer).

Then, the following primers were synthesized:

TM100inRV: gTC AAg gCg TTA CTC Tgg (SEQ ID NO: 14) based on the 5' nucleotide sequence data of the longest clone from TM100;

TM100inFW: CTg ggT gAg gAT CAC CTC (SEQ ID NO: 15) based on the 3' nucleotide sequence data of the same clone;

TM75inRV: gAT gTC TAC gTg CCC TAC (SEQ ID NO: 16) based on the 5' nucleotide sequence data of the longest clone from TM75; and TM75inFW: ACg ACT CAg AgA AgA ACT g (SEQ ID NO: 17) based on the 3' nucleotide sequence data of the same clone; and used for sequencing. Thus, both DNA sequences of the longest clones from TM100 and TM75 were determined, so that the total nucleotide sequence was determined.

The results showed that the cDNA encoding *Pleurotus cornucopiae* antifungal protein (from TM100 probe) consist of a total of 671 bases (SEQ ID NO: 1) encoding 143 amino acids (SEQ ID NO: 2). The N-terminal amino acid sequence determined from the purified protein corresponded to the amino acid residues 8-76 of the amino acid sequence of SEQ ID NO: 2. The amino acid sequence of SEQ ID NO: 2 and 67 amino acids directly determined from the purified protein were totally identical except for two unknown amino acids (corresponding to W 65 and S 73 in the amino acid sequence of SEQ ID NO: 2). This led to the conclusion that the cloned cDNA is derived from a gene encoding *Pleurotus cornucopiae* antifungal protein.

The N-terminal sequence of the protein determined from the cDNA sequence was not identical with the N-terminal sequence of the actually purified protein, i.e. L (leucine) after 7 amino acids following the initiation codon methionine was located at the N-terminus of the purified protein. This indicated that *Pleurotus cornucopiae* antifungal protein was translated as a precursor at first and then, the N-terminal leader sequence (7 amino acids) was truncated. The average molecular weight of the amino acid sequence of the putative mature protein (a sequence of 136 amino acids 8-143 of SEQ ID NO: 2) was 15158.4 as determined using a gene sequence analysis software program GENETYX-WIN ver 3.2 (Software Development Co., Ltd.), and the isoelectric point was calculated at 6.22. This molecular weight agreed well with the estimation (15 kDa) of the purified protein by SDS-PAGE. In addition, two putative glycosylation sites existed (N 21 and 71 of SEQ ID NO: 2).

On the other hand, the cDNA encoding a homolog of the *Pleurotus cornucopiae* antifungal protein (from TM75) consists of a total of 840 bases (SEQ ID NO: 3) encoding 141 amino acids (SEQ ID NO: 4). The cDNA contains three ATG codons at the 5' end, but when translation starts from the first and second ATG codons, a termination codon appears close behind them and only 12 and 31 amino acids can be encoded. Only when translation starts from the third ATG codon, 141 amino acids can be encoded. A termination codon TGA was located at 102 bp upstream of this ATG in the same reading frame. Thus, it is nearly certain that the third ATG is an initiation codon.

The molecular weight of the putative mature amino acid sequence (a sequence of 134 amino acids consisting of residues 8-141 of the amino acid sequence of SEQ ID NO: 4) was estimated at 14732.2, and the isoelectric point was calculated at 8.62. One putative glycosylation site existed (N 115 of SEQ ID NO: 4). The homology between the *Pleurotus cornucopiae* antifungal protein of the present invention and the homolog was 65.5% in amino acid and 64.5% in DNA (ORF 72.2%) as analyzed using GENETYX-WIN.

Homology searches were performed through GenBank databases using BLAST for the *Pleurotus cornucopiae*-derived antifungal protein of the present invention and the gene thereof as well as their homologs and proteins having an amino acid sequence encoded thereby. Database searches of the amino acid sequence of the *Pleurotus cornucopiae*-derived antifungal protein of the present invention (total amino acid sequence of SEQ ID NO: 2) found homologous sequences such as streptavidin v2 of *Streptomyces violaceus* (Accession No: □53533, Bayer et al. (1995) Biochim Biophys Acta 1263: pp. 60-66) and v1 (Accession No: Q53532), streptavidin of *Streptomyces avidinii* (Accession No.: P22629, Argarana et al. (1986) Nucleic Acids Res 14: pp. 1871-1882), etc. The homologies of these three sequences extend over 128 amino acids, and were 50%, 49% and 49%, respectively. Egg white avidin (Gope et al. (1987) Nucleic Acids Res 15: pp. 3595-3606) and several avidin-related proteins (Keinanen et al. (1994) Eur J Biochem 220: pp. 615-621) were also matched at lower homology degrees. A core streptavidin mutant w79f ChainB (Freitag et al. (1997) Protein Sci. 6: pp. 1157-1166) was also matched, which differs from streptavidin by only one amino acid and in which 36 N-terminal amino acids and 20 C-terminal amino acids of streptavidin are truncated. The homology was 51.7%.

These facts indicate that the present protein is a novel protein. Database searches of the amino acid sequence of the second *Pleurotus cornucopiae*-derived antifungal protein of the present invention (total amino acid sequence of SEQ ID NO: 4) showed homology degrees of 50%, 48% and 48% to streptavidin v2, v1 and streptavidin, respectively.

However, similar database searches using the DNA sequence of a gene encoding the first *Pleurotus cornucopiae*-derived antifungal protein (71-502 of SEQ ID NO: 1) and the DNA sequence of a gene encoding the second *Pleurotus cornucopiae*-derived antifungal protein (226-651 of SEQ ID NO: 3) found only several sequences showing homology in a very short range (23 bp) but not the DNA sequence of streptavidin. This means that the DNA sequences encoding the novel proteins of the present invention are not highly homologous to the DNA sequence of streptavidin on the DNA level.

The present antifungal protein was named "tamavidin" because it was a novel streptavidin-like protein purified from an edible mushroom *Pleurotus cornucopiae* (Tamogitake). The gene derived from the purified protein is called tam1, the protein having an amino acid sequence encoded thereby is called tamavidin 1, a homolog of tam1 is called tam 2, and the protein having an amino acid sequence encoded thereby is called tamavidin 2. When a genetic sequence analysis software program GENETYX-WIN ver 3.2 was used to analyze homology of the total amino acid sequences of the *Pleurotus cornucopiae* antifungal proteins of the present invention to streptavidin (which differs from streptavidins v2 and v1 by only 9 amino acids and 1 amino acid, respectively), the amino acid sequence of tamavidin 1 encoded by tam1 showed a homology (amino acid identity) of 46.7% and the amino acid sequence of tamavidin 2 encoded by tam2 showed 48.1%. The homology of the total DNA sequence (SEQ ID NOs: 1 and 3) to streptavidin was 53.8% (ORF 56.8%) for tam1 and 51.0% (ORF 57.3%) for tam2. The homology of the *Pleurotus cornucopiae* antifungal protein encoded by tam1 to egg white avidin was 31.2% in amino acid sequence and 42.4% in DNA sequence, and the homology of the *Pleurotus cornucopiae* antifungal protein encoded by tam2 to egg white avidin was 36.2% in amino acid sequence and 41.8% in DNA sequence.

Figure 7:
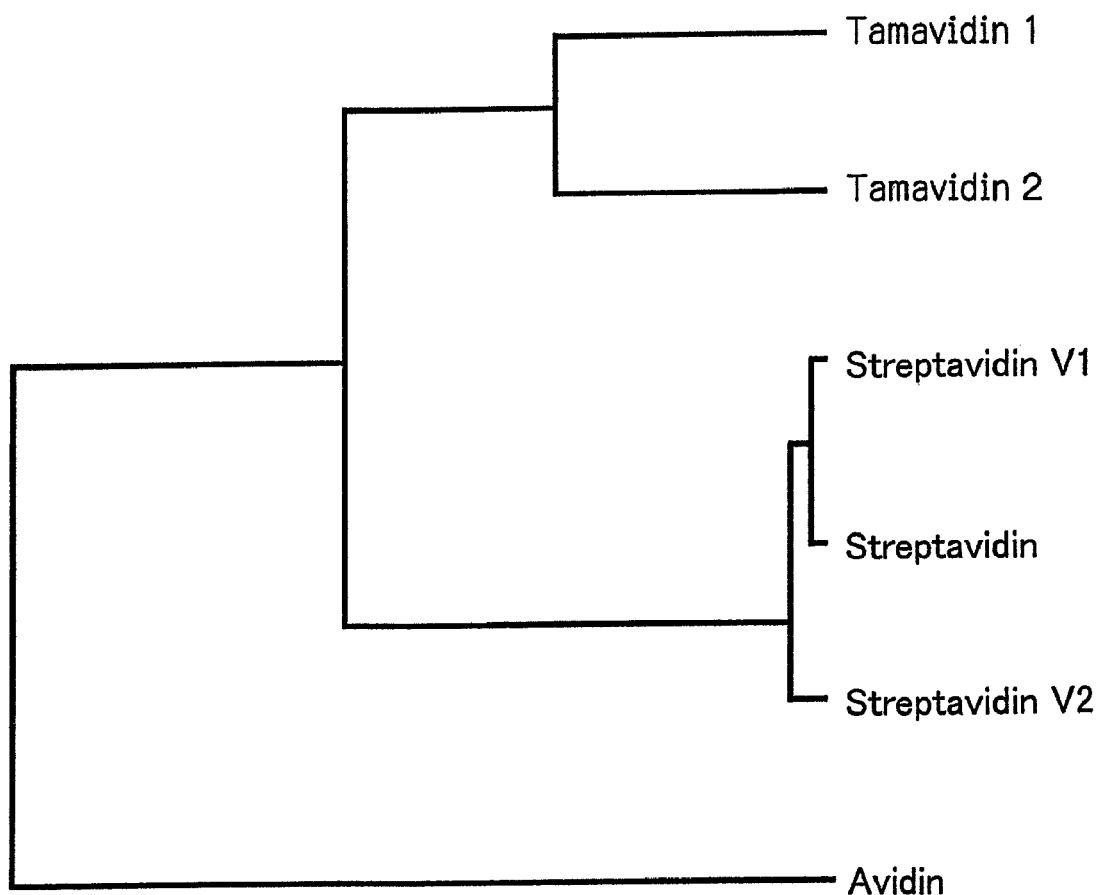
FIG. 7 shows a molecular taxonomic tree of the amino acid sequences (mature protein regions) of tamavidin 1 and tamavidin 2, streptavidin and its homolog, and avidin.

A molecular taxonomic tree of the amino acid sequences of the mature protein regions of tamavidin 1, tamavidin 2, streptavidin, streptavidin V1, streptavidin V2 and avidin was prepared by the UPGMA method using GENETYX-WIN. The results showed that tamavidin 1 and tamavidin 2 form a third group distinct from the streptavidin group and avidin group as shown in FIG. 7.

As compared with streptavidin, tamavidin 1 and tamavidin 2 of the present invention are truncated by 33 N-terminal amino acids, but all the tryptophan (W) residues (Gitlin et al. (1988) Biochem. J. 256: pp. 279-282) and tyrosine (Y) residues (Gitlin et al. (1990) Biochem. J. 269: pp. 527-530) possibly involved in binding to biotin are conserved (Y 34 and 45 and W 82, 98 and 110 in the amino acid sequence of SEQ ID NO: 2, and Y 34 and 45 and W 80, 96 and 108 in the amino acid sequence of SEQ ID NO: 4).

The average molecular weights of the regions supposed to be mature protein regions (stretches 8-143 of the amino acid sequence of SEQ ID NO: 2, and 8-141 of the amino acid sequence of SEQ ID NO: 4) were calculated at 15158.4 and 14732.2, respectively, close to the average molecular weights of mature streptavidin and mature avidin (16490.6 and 14342.9, respectively). These facts strongly suggest that not only tamavidin 1 encoded by tam1 but also tamavidin 2 encoded by tam2 is a protein having biotin-binding affinity.

Example 4

Experiments of Abolishment of an Antifungal Activity by Biotinylation

The antifungal proteins of the present invention are novel streptavidin-like proteins, suggesting that it binds to one of vitamins, D-biotin (vitamin H, Katayama Chemical). Rice blast is known to require biotin for its growth. These facts suggest that the present antifungal protein binds to free biotin present in assay media to induce biotin deficiency in the media, with the result that the growth of rice blast (*M. grisea*) is inhibited.

Figure 8:
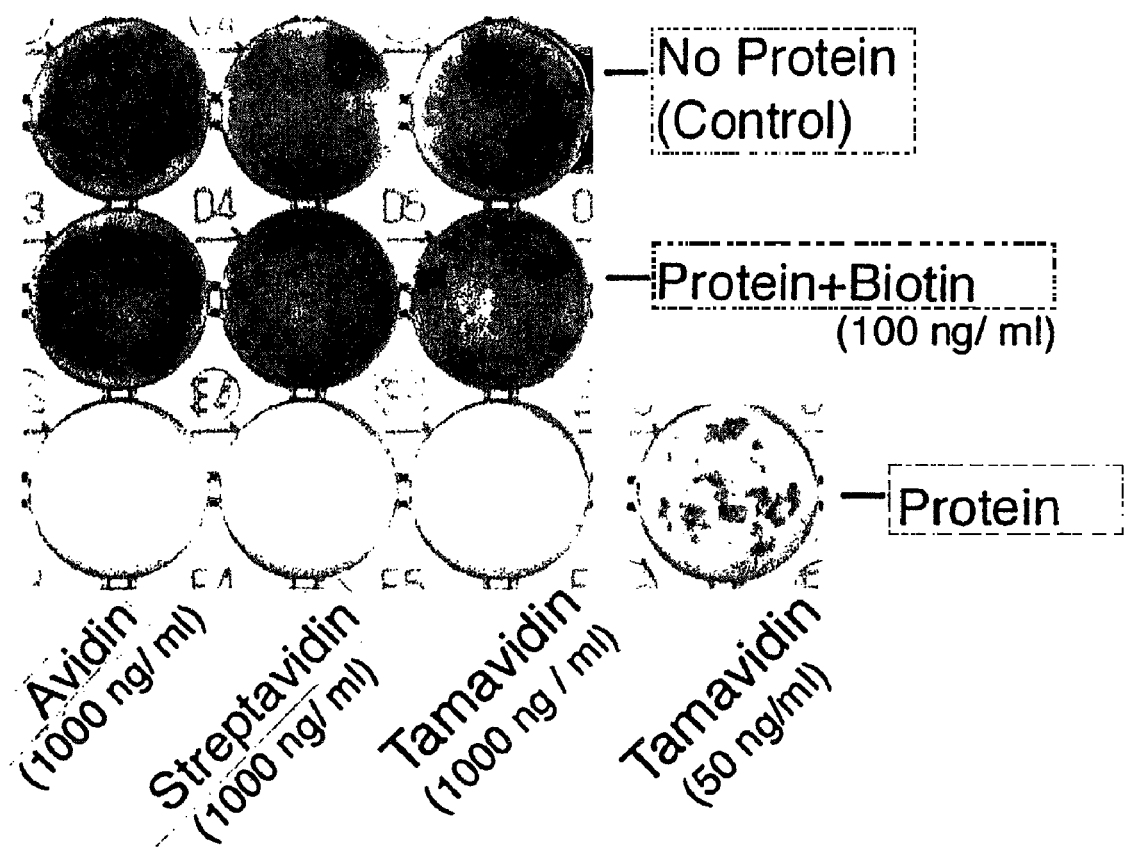
FIG. 8 shows the results of experiments of abolishment of an antifungal activity by addition of biotin. Spores of *M. grisea* suspended in ½ PD were placed in microtiter plates. Wells containing 1000 ng/ml of purified tamavidin 1, streptavidin and avidin, or wells containing 100 ng/ml biotin in addition to these proteins at the same concentrations, or wells containing no protein were prepared and incubated at 28° C. for 48 hours. Wells containing 50 ng/ml of purified tamavidin 1 are also shown.

FIG. 8 shows the results of experiments of abolishment of an antifungal activity by addition of biotin. Specifically, spores of *M. grisea* suspended in ½ PD were placed in microtiter plates. Wells containing 50 ng/ml or 1000 ng/ml of purified tamavidin 1, or wells containing 1000 ng/ml of tamavidin1 and 100 ng/ml of biotin, or control wells containing no protein were prepared and incubated at 28° C. for 48 hours.

As a result, the extension of hyphae of *M. grisea* was fairly inhibited in wells containing tamavidin 1 even at a concentration of 50 ng/ml as shown in FIG. 8. However, hyphae normally extended in wells containing both tamavidin 1 (1000 ng/ml) and biotin and control wells. Thus, an antifungal activity of the present antifungal protein was actually abolished by excessively adding biotin into the assay media. This is probably because a certain part of biotin excessively added bound to most of tamavidin 1 used for the assay to inactivate its antifungal activity.

Similar tests were performed on commercially available egg white avidin (Sigma) and streptavidin of *Streptmyces avidinii* (Sigma) at a concentration of 1000 ng/ml. The results showed that both proteins had the antifungal activity against *M. grisea* and the activity was abolished by biotin (FIG. 8).

Example 5

Biotin-binding Activity of Recombinant Tamavidin 2 Protein

1) Construction of an Expression Vector

Evaluations were performed as to find out whether or not tamavidin 2 encoded by tam2 gene, which is a gene isolated as a homolog of tam1 gene of the present invention, practically shows biotin-binding activity. Specifically, tam2 gene was inserted into *E. coli* to express recombinant tamavidin 2 and was examined as to find out whether or not this protein is purified on an iminobiotin column.

Initially, a primer pair was synthesized for amplifying the total ORF of tam2 gene obtained in Example 3 (bases 226-651 of SEQ ID NO: 3 in the Sequence Listing) by PCR.

```
TM75Bsp5:
5'-ACCAACATgTCAgACgTTCAA-3'       (SEQ ID NO: 18)

TM75Hin3:
5'-ATgAAAgCTTTTACTTCAACCTCgg-3'.  (SEQ ID NO: 19)
```

TM75Bsp5 contains a recognition site of restriction endonuclease BspLU 11I (underlined) and TM75Hin3 contains a recognition site of restriction endonuclease HindIII (underlined), respectively. These primers were used to perform PCR on a plasmid containing tam2 gene (pBluescript, Example 3 (6)) as a template. Using a programmed temperature control system PC-700 (ASTEK), 50 μl of a reaction solution containing 500 ng of template plasmid DNA, 5 μl of 10× Pyrobest buffer, 4 μl of 2.5 mM each dNTP, 10 pmoles of each primer and 0.5 μl of Pyrobest DNA polymerase (Takara) was run in 1 cycle at 94° C. for 3 min, 15 cycles of at 94° C. for 1 min, 50° C. for 1 min and 72° C. for 1 min, and then 1 cycle at 72° C. for 6 min.

The resulting PCR product was double digested with restriction endonucleases BspLU 11I (Roche) and HindIII (Takara) and subjected to gel-purification. The *E. coli* expression vector used was pTrc99A (Pharmacia LKB). This vector was double-digested with NcoI (Takara) and HindIII and gel-purified and ligated with the PCR product treated with restriction endonucleases as above, and then inserted into *E. coli* TB1. The nucleotide sequence of the inserted tam2 gene was confirmed.

2) Expression of the Recombinant Protein and Purification on a Biotin Column

A single colony of *E. coli* bearing the expression vector pTrc99A containing TB1 tam2 was inoculated into LB medium containing an antibiotic ampicillin and precultured to reach about $OD_{600}$=0.5. Then, IPTG was added at a final concentration of 1 mM to induce protein expression and cells were cultured by shaking at 37° C. for further 4.5 hours. The culture volume was 50 mL and a control without IPTG (Isopropyl-β-D (−)-thiogalactopyranoside, Wako Pure Chemical Industries) was also tested. Cultured cells were collected by centrifugation and stored at −80° C. until protein purification.

Tamavidin 2 was purified on iminobiotin referring to the method of Hofmann et al. Proc. Natl. Acad. Sci. USA 77: 4666-4668 (1980)). Cells were suspended in 1.5 mL of buffer A (50 mM CAPS (3-[Cyclohexylamino]-1-propanesulfonic acid, SIGMA), pH 11, 50 mM NaCl) and disrupted by sonication. After centrifugation, the supernatant was collected as total soluble protein. A column having a diameter of 0.5 cm and a height of 5 cm was charged with 0.5 mL of 2-Iminobiotin-Agarose (SIGMA) and equilibrated with buffer A. The total soluble protein was loaded on this iminobiotin agarose column. After the column was washed with 5 mL of 50 mM CAPS pH 11, 500 mM NaCl, tamavidin 2 was eluted with 1.5 mL of 50 mM NH$_4$OAC, pH 4.0. The total soluble protein and the fraction having passed through the column, the wash fraction and elution fraction were subjected to SDS-PAGE electrophoresis on 15% PAGEL (ATTO).

Figure 9:
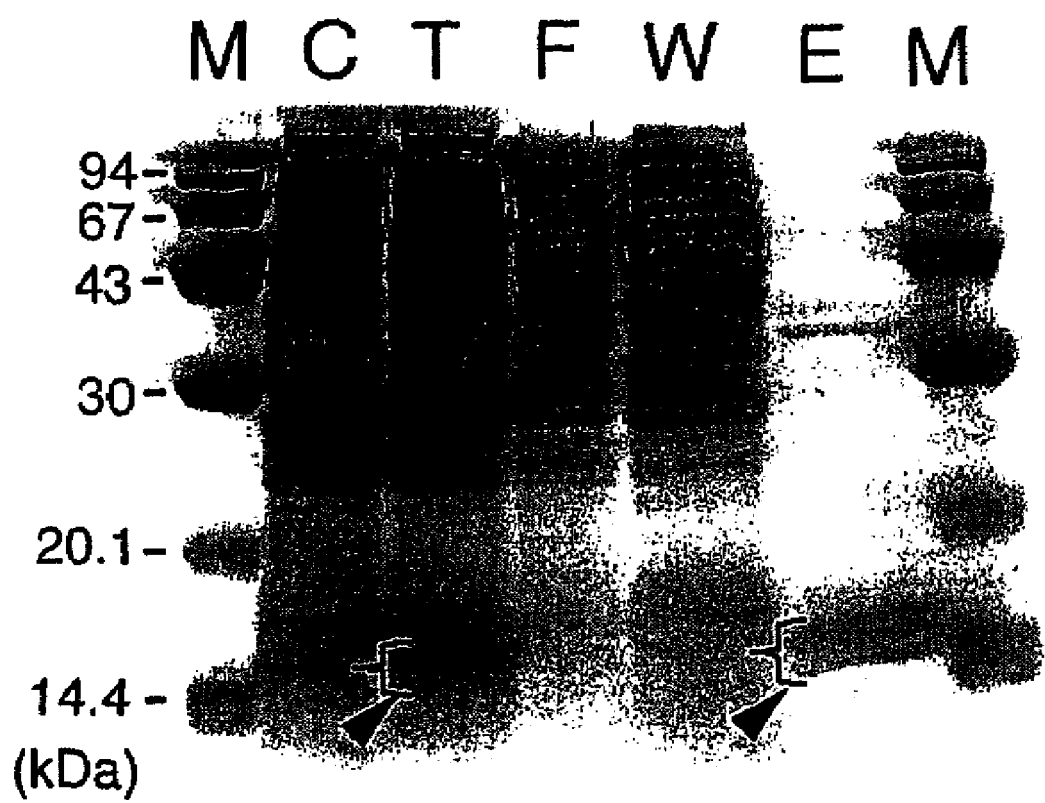
FIG. 9 shows purification of recombinant tamavidin 2 expressed in *E. coli* on an iminobiotin column. C represents the total soluble protein fraction of *E. coli*, which was not induced by IPTG, and T represents the total soluble protein fraction of *E. coli* induced by 1 mM IPTG. F represents the protein fraction having passed through the iminobiotin column without binding to the column, obtained from the total soluble protein fraction of *E. coli* induced by 1 mM IPTG, W represents the fraction eluted by washing the column, and E represents the fraction eluted with an acidic buffer. Arrows indicate tamavidin 2 protein (about 15 kDa), and M represents a molecular weight marker (LMW marker kit: Pharmacia LKB).

After migration, the protein was stained with Coomassie Brilliant Blue R-250 (Wako Pure Chemical Industries). The results are shown in FIG. 9. As shown in FIG. 9, the total soluble protein fraction induced by 1 mM IPTG (T) showed a band around 15 kDa, which was not found in the uninduced fraction (C). This molecular weight agreed well with the molecular weight of 15467 deduced from 141 amino acids encoded by tam2 gene.

In addition, this 15 kDa protein appeared in the fraction eluted with 50 mM NH$_4$OAC, pH 4.0 (E), but not in the fraction having passed through the biotin column (F) and the wash fraction of the column (W). The 15 kDa protein formed a major element in the elution fraction. This result shows that tamavidin 2 encoded by tam2 binds to biotin. The result also shows that it can be conveniently purified by the method shown above. The yield of recombinant tamavidin 2 expressed in *E. coli* obtained from a culture volume of 50 mL was about 1 mg.

Effects

Formulations containing as an active ingredient a protein element characterized by comprising a polypeptide consisting of the amino acid sequence of SEQ ID NO: 2 or 4 or a polypeptide consisting of a partial sequence thereof and capable of binding to biotin or a derivative thereof according to the present invention can be expected for use as antifungal agents.

Disease-resistant plants can also be created by integrating a DNA having the sequence of 71-502 or 92-502 of SEQ ID NO: 1 or a DNA having the sequence of 226-651 or 247-651 of SEQ ID NO: 3 of the present invention into an expression cassette containing a suitable constitutive promoter functional in a plant cell, an organ/time-specific promoter or an inducible promoter sequence responding to stress or pests and a terminator sequence functional in the plant cell and then introducing the cassette into the plant cell to give a regenerated individual. In this case, a DNA sequence encoding a signal sequence for transporting to small cellular organs or a signal sequence for extracellular secretion can also be linked to the DNA sequence encoding the antifungal protein of the present invention.

The proteins of the present invention can be produced and prepared in mass in cells of *E. coli*, yeasts, plants, insects or animals such as *Xenopus* by integrating a DNA sequence encoding the protein of the present invention into an expression vector capable of expressing foreign proteins in the cells. In this case, a DNA sequence encoding a signal sequence for transporting to small cellular organs or a signal sequence for extracellular secretion can also be linked to the DNA sequence encoding the antifungal protein of the present invention.

The strong interaction between the proteins of the present invention and biotin can be applied to various analytic techniques that are currently widely used with streptavidin and avidin.

The invention claimed is:

1. An isolated protein, wherein
said protein has an amino acid sequence as set forth in SEQ ID NO:4; or
said protein has an amino acid sequence with 95% or more homology to said sequence.

2. An isolated protein, wherein
said protein comprises the amino acid sequence 8-141 as set forth in SEQ ID NO:4; or
said protein has an amino acid sequence with 95% or more homology to said sequence.

3. An isolated protein, wherein
said protein has an amino acid sequence as set forth in SEQ ID NO:4; or
said protein has an amino acid sequence with 90% or more homology to said sequence and with the tyrosine (Y) residues at 34 and 45, and the tryptophan (w) residues at 80, 96 and 108 in the amino acid sequence of SEQ ID NO:4 remaining unchanged.

4. An isolated protein according to claim 3 having an amino acid sequence with 95% or more homology to SEQ ID NO: 4.

5. An isolated protein, wherein
said protein has an amino acid sequence 8-141 as set forth in SEQ ID NO:4; or
said protein has an amino acid sequence with 90% or more homology to said sequence and with the tyrosine (Y) residues at 34 and 45, and the tryptophan (w) residues at 80, 96 and 108 in the amino acid sequence of SEQ ID NO:4 remaining unchanged.

6. An isolated protein according to claim 5 having an amino acid sequence with 95% or more homology to sequence 8-141 as set forth in SEQ ID NO:4.

7. The isolated protein of any one of claims 1, 2, 3, 4, 5, and 6, wherein said protein exhibits a biotin-binding activity.

8. A recombinant protein produced by a transformant obtained by introducing a recombinant vector comprising a gene encoding the protein according to any one of claims 1, 2, 3, 4, 5, and 6 to a host cell, culturing the host cell under suitable conditions for expression, and isolating the expressed recombinant protein.

9. The isolated protein of claim 1, which has the amino acid sequence as set forth in SEQ ID NO: 4.

10. The isolated protein of claim 2, which comprises the amino acid sequence 8-141 as set forth in SEQ ID NO; 4.

11. The isolated protein of claim 5, which has the amino acid sequence 8-141 as set forth in SEQ ID NO: 4.

* * * * *

UNITED STATES PATENT AND TRADEMARK OFFICE
CERTIFICATE OF CORRECTION

PATENT NO. : 7,713,531 B2
APPLICATION NO. : 12/369587
DATED : May 11, 2010
INVENTOR(S) : Yoshimitsu Takakura Page 1 of 1

It is certified that error appears in the above-identified patent and that said Letters Patent is hereby corrected as shown below:

On the cover page item "(62) Division of application No. 10/471,422, filed as application No. PCT/JP02/02295 on Mar. 12, 2002." should read --(62) Division of application No. 10/471,422 filed on Sep. 11, 2003, which is the National Stage of PCT/JP02/02295 filed on Mar. 12, 2002.--

Signed and Sealed this

Twenty-ninth Day of June, 2010

David J. Kappos
*Director of the United States Patent and Trademark Office*

SEQUENCE LISTING

```
<160> NUMBER OF SEQ ID NOS: 19

<210> SEQ ID NO 1
<211> LENGTH: 671
<212> TYPE: DNA
<213> ORGANISM: Pleurotus cornucopiae
<220> FEATURE:
<221> NAME/KEY: CDS
<222> LOCATION: (71)...(502)

<400> SEQUENCE: 1
gcccagagag accatctata acctctgcgt ccaaaccttc attgaaagct tcaaccccca      60
gtcccccatc atg aaa gac gtc caa tct ctc ctc acc gga acc tgg tac       109
            Met Lys Asp Val Gln Ser Leu Leu Thr Gly Thr Trp Tyr
              1               5                  10 aat gaa ctc ggc tca aca atg aat ttg act gca aat aaa gac ggt tcg       157
Asn Glu Leu Gly Ser Thr MET Asn Leu Thr Ala Asn Lys Asp Gly Ser
     15                  20                  25 ctc acc gga acg tac cac tcc aac gtc ggc gag gtt ccc cca act tat       205
Leu Thr Gly Thr Tyr His Ser Asn Val Gly Glu Val Pro Pro Thr Tyr
 30                  35                  40                  45 cac ctt tct ggc cgg tac aac ctc cag ccc ccc tcg ggt caa ggc gtt       253
His Leu Ser Gly Arg Tyr Asn Leu Gln Pro Pro Ser Gly Gln Gly Val
                 50                  55                  60 act ctg gga tgg gcg gtg tct ttc gaa aac act agt gcg aat gtt cat       301
Thr Leu Gly Trp Ala Val Ser Phe Glu Asn Thr Ser Ala Asn Val His
```

```
                    65                  70                  75
tct gtc tca aca tgg agc ggg cag tac ttc tct gaa ccc gcc gag gtg    349
Ser Val Ser Thr Trp Ser Gly Gln Tyr Phe Ser Glu Pro Ala Glu Val
            80                  85                  90 atc ctc acc cag tgg ctg ttg tca agg agc tct gag cgc gaa gat ttg    397
Ile Leu Thr Gln Trp Leu Leu Ser Arg Ser Ser Glu Arg Glu Asp Leu
        95                 100                 105 tgg cag tcc acc cat gtg ggg cat gat gag ttc agc aag aca aag cca    445
Trp Gln Ser Thr His Val Gly His Asp Glu Phe Ser Lys Thr Lys Pro
110                 115                 120                 125 acc aag gag aag att gcc cag gct caa ctc ctt cgt cgc ggg ttg aag    493
Thr Lys Glu Lys Ile Ala Gln Ala Gln Leu Leu Arg Arg Gly Leu Lys
                130                 135                 140 ttc gag tga acctgattca cgaaaaattc cgtctatcca acgttggaga tgactccac  551
Phe Glu
    143 ctcaagttgt gaatgtttgc tcatttgtac cgaatctgta cgacaagttt gtctgccacc  611 atgtacatcg caaagaatta tcaagaaact ccatgacctg ccaaaaaaaa aaaaaaaaaa  671

<210> SEQ ID NO 2
<211> LENGTH: 143
<212> TYPE: PRT
<213> ORGANISM: Pleurotus cornucopiae

<400> SEQUENCE: 2

Met Lys Asp Val Gln Ser Leu Leu Thr Gly Thr Trp Tyr
  1               5                  10

Asn Glu Leu Gly Ser Thr MET Asn Leu Thr Ala Asn Lys Asp Gly Ser
         15                  20                  25

Leu Thr Gly Thr Tyr His Ser Asn Val Gly Glu Val Pro Pro Thr Tyr
 30                  35                  40                  45

His Leu Ser Gly Arg Tyr Asn Leu Gln Pro Pro Ser Gly Gln Gly Val
                 50                  55                  60

Thr Leu Gly Trp Ala Val Ser Phe Glu Asn Thr Ser Ala Asn Val His
             65                  70                  75

Ser Val Ser Thr Trp Ser Gly Gln Tyr Phe Ser Glu Pro Ala Glu Val
         80                  85                  90

Ile Leu Thr Gln Trp Leu Leu Ser Arg Ser Ser Glu Arg Glu Asp Leu
     95                 100                 105

Trp Gln Ser Thr His Val Gly His Asp Glu Phe Ser Lys Thr Lys Pro
110                 115                 120                 125

Thr Lys Glu Lys Ile Ala Gln Ala Gln Leu Leu Arg Arg Gly Leu Lys
                130                 135                 140

Phe Glu

<210> SEQ ID NO 3
<211> LENGTH: 840
<212> TYPE: DNA
<213> ORGANISM: Pleurotus cornucopiae
<220> FEATURE:
<221> NAME/KEY: CDS
<222> LOCATION: (226)...(651)

<400> SEQUENCE: 3
gtggactctt gcgcgggcag gtacattcac aggtcgtgca ggttgtggga gtattcagtg   60
gctcagactc ttgtgctgac gggtatagat tcaagccgtg caggttgt gggagtactc     120 agagggtgag tgattgaatg gaagcacatc ggcgctggtt tcaagccgag aattgaggaa  180
```

-continued

```
gtaatactcc aagccgatga gaggttacag agatcctcta ccacc atg tca gac gtt       237
                                                  Met Ser Asp Val
                                                   1 caa tct tca ctc acc gga acc tgg tac aat gaa ctc aac tcc aag atg         285
Gln Ser Ser Leu Thr Gly Thr Trp Tyr Asn Glu Leu Asn Ser Lys Met
 5               10                  15                  20 gaa ttg act gca aac aaa gac ggt act ctc act gga aag tac ctc tcc         333
Glu Leu Thr Ala Asn Lys Asp Gly Thr Leu Thr Gly Lys Tyr Leu Ser
                 25                  30                  35 aaa gtt ggg gat gtc tac gtg ccc tac cca ctc tct ggt cgc tat aac         381
Lys Val Gly Asp Val Tyr Val Pro Tyr Pro Leu Ser Gly Arg Tyr Asn
             40                  45                  50 ctc caa ccc ccc gcg gga caa ggc gtc gct ctt ggg tgg gcg gta tcc         429
Leu Gln Pro Pro Ala Gly Gln Gly Val Ala Leu Gly Trp Ala Val Ser
             55                  60                  65 tgg gag aac agt aaa att cat tcc gct acg aca tgg agc gga cag ttc         477
Trp Glu Asn Ser Lys Ile His Ser Ala Thr Thr Trp Ser Gly Gln Phe
         70                  75                  80 ttc tct gag tcg tct cca gtg att ctt act cag tgg ttg ttg tca tcg         525
Phe Ser Glu Ser Ser Pro Val Ile Leu Thr Gln Trp Leu Leu Ser Ser
85                  90                  95                  100 agc act gcg cgt ggg gac gta tgg gaa tcc aca ctt gtg ggg aat gat         573
Ser Thr Ala Arg Gly Asp Val Trp Glu Ser Thr Leu Val Gly Asn Asp
                 105                 110                 115 tcg ttt aca aag acg gcg ccg act gag cag cag atc gct cat gct caa         621
Ser Phe Thr Lys Thr Ala Pro Thr Glu Gln Gln Ile Ala His Ala Gln
                 120                 125                 130 ctc cat tgt cgc gca ccg agg ttg aag taa cgagggtcat cgcaaacaaa ccc       674
Leu His Cys Arg Ala Pro Arg Leu Lys
                 135                 140 catcggtctt gaccggtgat ccaaccccaa ggtctaatca atgccggatg actccatttg       734
aggatgtgaa ttagttgcca tttgtatgac ttgatttgtc tgttgtgtag tatcggatta       794
agaatcacat ctcgttaacc ttcaaaaaaa aaaaaaaaaa aaaaaa                      840
```

<210> SEQ ID NO 4
<211> LENGTH: 141
<212> TYPE: PRT
<213> ORGANISM: Pleurotus cornucopiae

<400> SEQUENCE: 4

Met Ser Asp Val
 1

Gln Ser Ser Leu Thr Gly Thr Trp Tyr Asn Glu Leu Asn Ser Lys Met
 5               10                  15                  20

Glu Leu Thr Ala Asn Lys Asp Gly Thr Leu Thr Gly Lys Tyr Leu Ser
                 25                  30                  35

Lys Val Gly Asp Val Tyr Val Pro Tyr Pro Leu Ser Gly Arg Tyr Asn
             40                  45                  50

Leu Gln Pro Pro Ala Gly Gln Gly Val Ala Leu Gly Trp Ala Val Ser
             55                  60                  65

Trp Glu Asn Ser Lys Ile His Ser Ala Thr Thr Trp Ser Gly Gln Phe
         70                  75                  80

Phe Ser Glu Ser Ser Pro Val Ile Leu Thr Gln Trp Leu Leu Ser Ser
85                  90                  95                  100

Ser Thr Ala Arg Gly Asp Val Trp Glu Ser Thr Leu Val Gly Asn Asp
                 105                 110                 115

```
Ser Phe Thr Lys Thr Ala Pro Thr Glu Gln Gln Ile Ala His Ala Gln
                120                 125                 130

Leu His Cys Arg Ala Pro Arg Leu Lys
        135                 140

<210> SEQ ID NO 5
<211> LENGTH: 44
<212> TYPE: PRT
<213> ORGANISM: Pleurotus cornucopiae
<220> FEATURE:
<221> NAME/KEY: misc_feature
<222> LOCATION: (2)..(2)
<223> OTHER INFORMATION: Xaa represents unknown amino acid residue
<220> FEATURE:
<221> NAME/KEY: misc_feature
<222> LOCATION: (4)..(4)
<223> OTHER INFORMATION: Xaa represents unknown amino acid residue
<220> FEATURE:
<221> NAME/KEY: misc_feature
<222> LOCATION: (11)..(12)
<223> OTHER INFORMATION: Xaa represents unknown amino acid residue
<220> FEATURE:
<221> NAME/KEY: misc_feature
<222> LOCATION: (24)..(24)
<223> OTHER INFORMATION: Xaa represents unknown amino acid residue
<220> FEATURE:
<221> NAME/KEY: misc_feature
<222> LOCATION: (36)..(37)
<223> OTHER INFORMATION: Xaa represents unknown amino acid residue

<400> SEQUENCE: 5

Leu Xaa Gly Xaa Trp Tyr Asn Glu Leu Gly Xaa Xaa Met Asn Leu Thr
  1               5                  10                  15

Ala Asn Lys Asp Gly Ser Leu Xaa Gly Thr Tyr His Ser Asn Val Gly
             20                  25                  30

Glu Val Pro Xaa Xaa Tyr His Leu Ala Gly Arg Tyr
            35                  40

<210> SEQ ID NO 6
<211> LENGTH: 50
<212> TYPE: PRT
<213> ORGANISM: Pleurotus cornucopiae
<220> FEATURE:
<221> NAME/KEY: misc_feature
<222> LOCATION: (39)..(39)
<223> OTHER INFORMATION: Xaa represents unknown amino acid residue
<220> FEATURE:
<221> NAME/KEY: misc_feature
<222> LOCATION: (47)..(47)
<223> OTHER INFORMATION: Xaa represents unknown amino acid residue

<400> SEQUENCE: 6

Asp Gly Ser Leu Thr Gly Thr Tyr His Ser Asn Val Gly Glu Val Pro
  1               5                  10                  15

Pro Thr Tyr His Leu Ser Gly Arg Tyr Asn Leu Gln Pro Pro Ser Gly
             20                  25                  30

Gln Gly Val Thr Leu Gly Xaa Ala Val Ser Phe Glu Asn Thr Xaa Ala
         35                  40                  45

Asn Val
     50

<210> SEQ ID NO 7
<211> LENGTH: 21
<212> TYPE: PRT
<213> ORGANISM: Pleurotus cornucopiae

<400> SEQUENCE: 7
```

```
Leu Thr Gly Thr Trp Tyr Asn Glu Leu Gly Ser Thr Met Asn Leu Thr
  1               5                  10                  15

Ala Asn Lys Asp Gly
             20
```

<210> SEQ ID NO 8
<211> LENGTH: 23
<212> TYPE: PRT
<213> ORGANISM: Pleurotus cornucopiae
<220> FEATURE:
<221> NAME/KEY: misc_feature
<222> LOCATION: (5)..(5)
<223> OTHER INFORMATION: Xaa represents unknown amino acid residue
<220> FEATURE:
<221> NAME/KEY: misc_feature
<222> LOCATION: (13)..(13)
<223> OTHER INFORMATION: Xaa represents unknown amino acid residue
<220> FEATURE:
<221> NAME/KEY: misc_feature
<222> LOCATION: (19)..(19)
<223> OTHER INFORMATION: Xaa represents unknown amino acid residue
<220> FEATURE:
<221> NAME/KEY: misc_feature
<222> LOCATION: (22)..(22)
<223> OTHER INFORMATION: Xaa represents unknown amino acid residue

<400> SEQUENCE: 8

```
Leu Thr Gly Thr Xaa Tyr Asn Glu Leu Gly Ser Thr Xaa Asn Leu Thr
  1               5                  10                  15

Ala Asn Xaa Asp Gly Xaa Leu
             20          23
```

<210> SEQ ID NO 9
<211> LENGTH: 69
<212> TYPE: PRT
<213> ORGANISM: Pleurotus cornucopiae
<220> FEATURE:
<221> NAME/KEY: misc_feature
<222> LOCATION: (58)..(58)
<223> OTHER INFORMATION: Xaa represents unknown amino acid residue
<220> FEATURE:
<221> NAME/KEY: misc_feature
<222> LOCATION: (66)..(66)
<223> OTHER INFORMATION: Xaa represents unknown amino acid residue

<400> SEQUENCE: 9

```
Leu Thr Gly Thr Trp Tyr Asn Glu Leu Gly Ser Thr Met Asn Leu Thr
  1               5                  10                  15

Ala Asn Lys Asp Gly Ser Leu Thr Gly Thr Tyr His Ser Asn Val Gly
             20                  25                  30

Glu Val Pro Pro Thr Tyr His Leu Ser Gly Arg Tyr Asn Leu Gln Pro
         35                  40                  45

Pro Ser Gly Gln Gly Val Thr Leu Gly Xaa Ala Val Ser Phe Glu Asn
     50                  55                  60

Thr Xaa Ala Asn Val
 65
```

<210> SEQ ID NO 10
<211> LENGTH: 19
<212> TYPE: DNA
<213> ORGANISM: Artificial Sequence
<220> FEATURE:
<223> OTHER INFORMATION: Degenerate primer TMR1
<220> FEATURE:
<221> NAME/KEY: misc_feature
<222> LOCATION: (3)..(3)
<223> OTHER INFORMATION: n is a, c, g, or t
<220> FEATURE:

```
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 10
acnggnacnt ggtayaayg                                              19

<210> SEQ ID NO 11
<211> LENGTH: 20
<212> TYPE: DNA
<213> ORGANISM: Artificial Sequence
<220> FEATURE:
<223> OTHER INFORMATION: Degenerate primer TMR2
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is inosine
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 11
garytnggnw snacnatgaa                                             20

<210> SEQ ID NO 12
<211> LENGTH: 18
<212> TYPE: DNA
<213> ORGANISM: Artificial Sequence
<220> FEATURE:
<223> OTHER INFORMATION: Degenerate primer TMF1
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is inosine
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is a, c, g, or t

<400> SEQUENCE: 12
gtrttytcra answnacn                                               18
```

<210> SEQ ID NO 13
<211> LENGTH: 20
<212> TYPE: DNA
<213> ORGANISM: Artificial Sequence
<220> FEATURE:
<223> OTHER INFORMATION: Degenerate primer TMF2
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is inosine
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 13
ccnarngtna cnccytgncc         20

<210> SEQ ID NO 14
<211> LENGTH: 18
<212> TYPE: DNA
<213> ORGANISM: Artificial Sequence
<220> FEATURE:
<223> OTHER INFORMATION: Primer TM100inRV

<400> SEQUENCE: 14
gtcaaggcgt tactctgg         18

<210> SEQ ID NO 15
<211> LENGTH: 18
<212> TYPE: DNA
<213> ORGANISM: Artificial Sequence
<220> FEATURE:
<223> OTHER INFORMATION: Primer TM100inFW

<400> SEQUENCE: 15
ctgggtgagg atcacctc         18

<210> SEQ ID NO 16
<211> LENGTH: 18
<212> TYPE: DNA
<213> ORGANISM: Artificial Sequence
<220> FEATURE:
<223> OTHER INFORMATION: Primer TM75inRV

<400> SEQUENCE: 16
gatgtctacg tgccctac         18

<210> SEQ ID NO 17

```
<211> LENGTH: 19
<212> TYPE: DNA
<213> ORGANISM: Artificial Sequence
<220> FEATURE:
<223> OTHER INFORMATION: Primer TM75inFW

<400> SEQUENCE: 17
acgactcaga gaagaactg                                                    19

<210> SEQ ID NO 18
<211> LENGTH: 21
<212> TYPE: DNA
<213> ORGANISM: Artificial Sequence
<220> FEATURE:
<223> OTHER INFORMATION: Primer TM75Bsp5

<400> SEQUENCE: 18
accaacatgt cagacgttca a                                                 21

<210> SEQ ID NO 19
<211> LENGTH: 25
<212> TYPE: DNA
<213> ORGANISM: Artificial Sequence
<220> FEATURE:
<223> OTHER INFORMATION: Primer TM75Hin3

<400> SEQUENCE: 19
atgaaagctt ttacttcaac ctcgg                                             25
```